United States Patent
Ahmed et al.

(10) Patent No.: US 12,161,671 B2
(45) Date of Patent: Dec. 10, 2024

(54) IMMUNE CELLS WITH DNMT3A GENE MODIFICATIONS AND METHODS RELATED THERETO

(71) Applicants: Emory University, Atlanta, GA (US); St. Jude Children's Hospital, Inc., Memphis, TN (US)

(72) Inventors: Rafi Ahmed, Atlanta, GA (US); Benjamin Youngblood, Decatur, GA (US)

(73) Assignees: Emory University, Atlanta, GA (US); St. Jude Children's Research Hospital, Inc., Memphis, TN (US)

( * ) Notice: Subject to any disclaimer, the term of this patent is extended or adjusted under 35 U.S.C. 154(b) by 708 days.

(21) Appl. No.: 17/330,378

(22) Filed: May 25, 2021

(65) Prior Publication Data

US 2021/0275592 A1    Sep. 9, 2021

Related U.S. Application Data

(62) Division of application No. 15/773,783, filed as application No. PCT/US2016/060627 on Nov. 4, 2016, now Pat. No. 11,020,430.

(60) Provisional application No. 62/250,546, filed on Nov. 4, 2015.

(51) Int. Cl.
| | |
|---|---|
| *A61K 35/17* | (2015.01) |
| *A61P 31/14* | (2006.01) |
| *A61P 35/00* | (2006.01) |
| *C07K 14/005* | (2006.01) |
| *C07K 14/705* | (2006.01) |
| *C12N 5/0783* | (2010.01) |
| *C12N 9/10* | (2006.01) |
| *C12N 15/85* | (2006.01) |

(52) U.S. Cl.
CPC .............. *A61K 35/17* (2013.01); *A61P 31/14* (2018.01); *A61P 35/00* (2018.01); *C07K 14/005* (2013.01); *C07K 14/70596* (2013.01); *C12N 5/0636* (2013.01); *C12N 5/0638* (2013.01); *C12N 9/1007* (2013.01); *C12Y 201/01037* (2013.01); *C12N 2510/00* (2013.01); *C12N 2740/16033* (2013.01); *C12N 2740/16111* (2013.01)

(58) Field of Classification Search
None
See application file for complete search history.

(56) References Cited

U.S. PATENT DOCUMENTS

| | | | | |
|---|---|---|---|---|
| 2009/0217401 A1* | 8/2009 | Korman | ........... | A61K 39/39558 536/23.53 |
| 2014/0120622 A1* | 5/2014 | Gregory | ................... | C12N 9/22 435/325 |

OTHER PUBLICATIONS

Thomas et al (J of Biolog. Chemistry, 2012, v.287,p. 22900-22909.*
Ahn et al. Demethylation of the PD-1 Promoter Is Imprinted during the Effector Phase of CD8 T Cell Exhaustion, J Virol ,2016, 90:8934-8946.
Gamper et al. Identification of DNA Methyltransferase 3a as a T Cell Receptor-Induced Regulator of Th1 and Th2 Differentiation, The Journal of Immunology, 2009, 183: 2267-2276.
Garfall et al. Chimeric Antigen Receptor T Cells against CD19 for Multiple Myeloma, N Engl J Med 2015, 373:1040-7.
Ghoneim et al. De Novo Epigenetic Programs Inhibit PD-1 Blockade-Mediated T Cell Rejuvenation, Cell, 2017, 170, 142-157.
Gill et al. Going viral: chimeric antigen receptor T-cell therapy for hematological malignancies, Immunological Reviews 2015, vol. 263: 68-89.
John et al. Anti-PD-1 Antibody Therapy Potently Enhances the Eradication of Established Tumors by Gene-Modified T Cells, Clin Cancer Res, 2013, 19(20); 5636-46.
Liu et al. Novel CD4-Based Bispecific Chimeric Antigen Receptor Designed for Enhanced Anti-HIV Potency and Absence of HIV Entry Receptor Activity, J Virol, 2015, 89:6685-6694.
Mali et al. RNA-Guided Human Genome Engineering via Cas9, Science. 2013, 339(6121): 823-826.
Milone et al. Chimeric Receptors Containing CD137 Signal Transduction Domains Mediate Enhanced Survival of T Cells and Increased Antileukemic Efficacy In Vivo, Molecular Therapy, 2009, 17(8) 1453-1464.
Park et al. Treating cancer with genetically engineered T cells, Trends in Biotechnology, 2011, vol. 29, No. 11.
Pauken et al. Overcoming T cell exhaustion in infection and cancer, Trends Immunol, 2015, 36(4): 265-276.
Sather et al. Efficient modification of CCR5 in primary human hematopoietic cells using a megaTAL nuclease and AAV donor template, Sci Transl Med, 2015, 7(307):307ra156.
Strommes et al. Re-adapting T cells for cancer therapy: from mouse models to clinical trials, Immunological Reviews 2014 Vol. 257: 145-164.

(Continued)

*Primary Examiner* — Michail A Belyavskyi
(74) *Attorney, Agent, or Firm* — Emory Patent Group

(57) ABSTRACT

This disclosure relates to the genetic modification of DNMT3A gene in immune cells. In certain embodiments, the modified immune cells may be used in adoptive T cells therapies to enhance immune responses against cancer or chronic infections. In certain embodiments, the disclosure relates to deleting, changing, or inserting nucleotides within the DNMT3A gene in immune cells, e.g., human CD8 T cells, such that the DNMT3A gene product does not function for methylation. In certain embodiments, modification of the DNMT3A gene provides an improvement in antigen-specific T cells functions and/or an enhancement of the longevity of the cells.

10 Claims, 16 Drawing Sheets

Specification includes a Sequence Listing.

(56) References Cited

OTHER PUBLICATIONS

Tebas et al. Gene Editing of CCR5 in Autologous CD4 T Cells of Persons Infected with HIV, N Engl J Med, 2014, 370:901-10.
Yang et al. DNMT3A in haematological malignancies, Nat Rev Cancer, 2015, 15(3):152-65.
Youngblood et al. Chronic virus infection enforces demethylation of the locus that encodes PD-1 in antigen-specific CD8+ T cells, Immunity, 2011, 35(3): 400-412.
Youngblood et al. Memory CD8 T cell transcriptional plasticity, F1000Prime Reports 2015, 7:38.
Youngblood et al. Dnmt3a mediated de novo DNA methylation programming enforces T cell exhaustion (RM14P.451), J Immunol, 2015, 194(1 Supplement) 198.11.
Youngblood et al. Effector CD8 T cells dedifferentiate into long-lived memory cells, Nature, 2017, 552, 404-409.
Youngblood et al. De novo DNA methylation programs restrain T cell rejuvenation during immune checkpoint plockade therapy, J Immunol, 2018 (1 Supp) 57.21.
Youngblood et al. De novo DNA methylation programs regulated T cell exhaustion and limit T cell-based Immunotherapies, 2019, 202, (1 Supp) 134.14.
Zamora et al. Pediatric patients with acute lymphoblastic leukemia generate abundant and functional neoantigen-specific CD8+ T cell responses, Sci. Transl. Med. 2019, 11, eaat8549.

\* cited by examiner

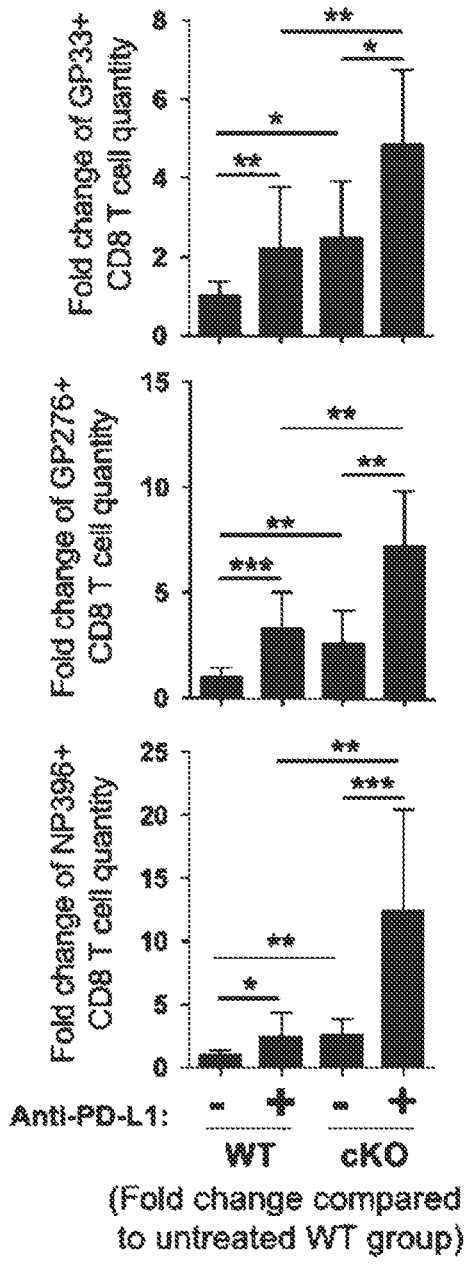
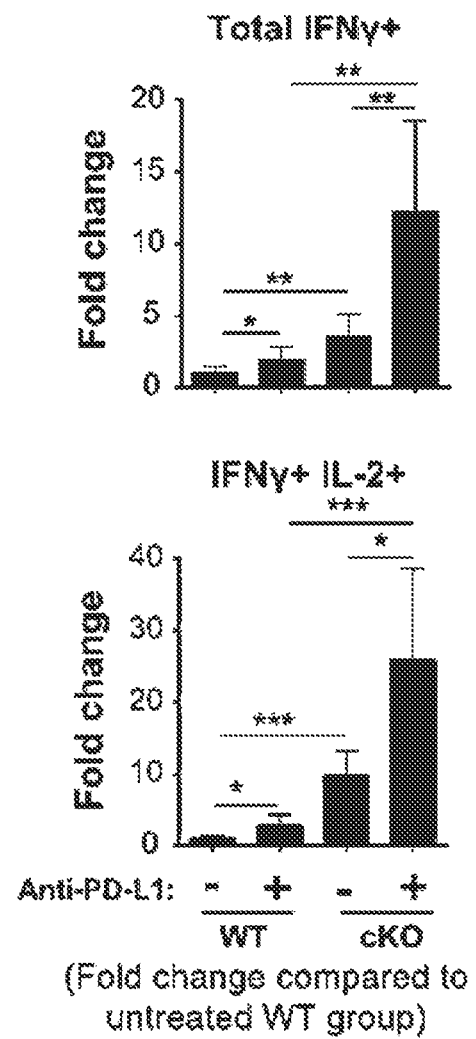
FIG. 5B
FIG. 5C

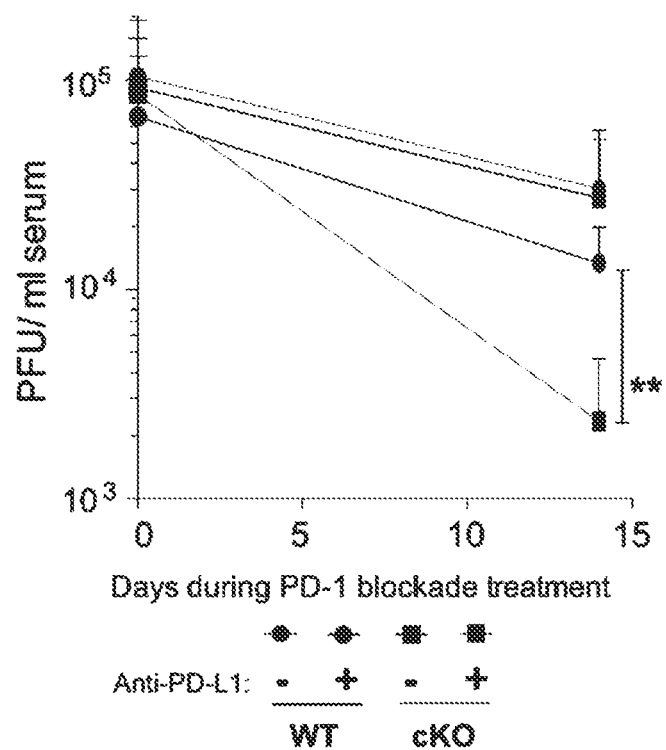
FIG. 5D
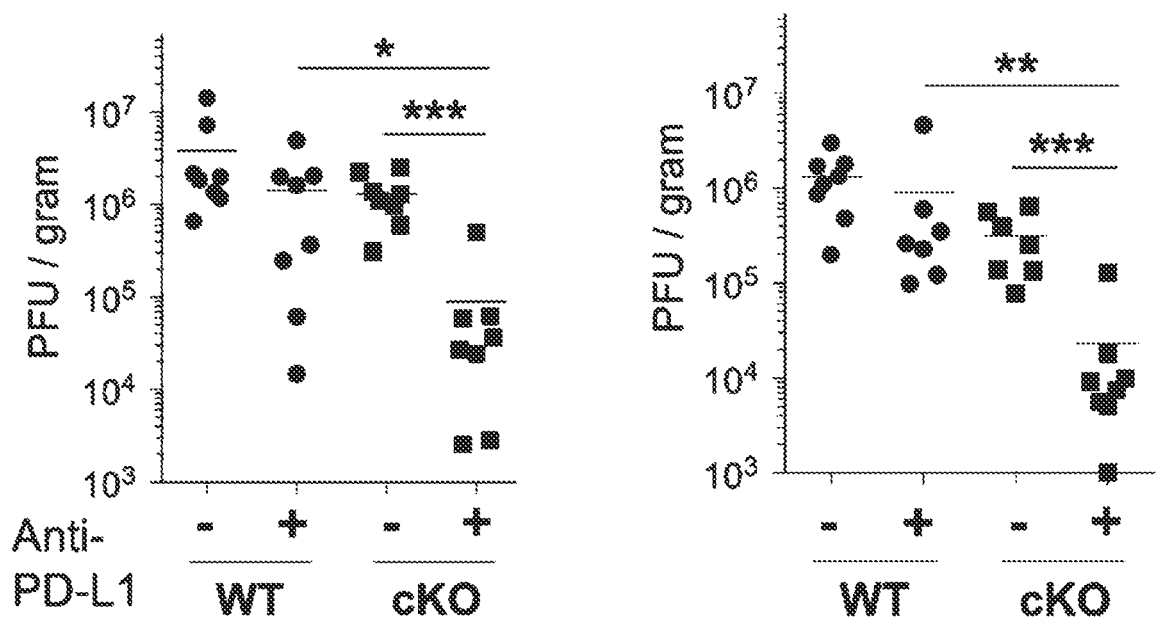
FIG. 5E
FIG. 5F

SEQUENCE LISTING

<160> NUMBER OF SEQ ID NOS: 2

<210> SEQ ID NO 1
<211> LENGTH: 17
<212> TYPE: DNA
<213> ORGANISM: Artificial
<220> FEATURE:
<223> OTHER INFORMATION: Synthetic

<400> SEQUENCE: 1
gcatgatgcg cggccca                                                17

<210> SEQ ID NO 2
<211> LENGTH: 381
<212> TYPE: DNA
<213> ORGANISM: Artificial
<220> FEATURE:
<223> OTHER INFORMATION: Synthetic

<400> SEQUENCE: 2
gtggaggtgc agaacaagcc catgattgaa tgggccctgg ggggcttcca gccttctggc      60
cctaagggcc tggagccacc agaagaagag aagaatccct acaaagaagt gtacacggac     120
atgtgggtgg aacctgaggc agctgcctac gcaccacctc caccagccaa aaagcccgg      180 aagagcacag cggagaagcc caaggtcaag gagattattg atgagcgcac aagagagcgg     240
ctggtgtacg aggtgcggca gaagtgccgg aacattgagg acatctgcat ctcctgtggg     300
agcctcaatg ttaccctgga acaccccctc ttcgttggag gaatgtgcca aaactgcaag     360
aactgctttc tggagtgtgc g                                              381

IMMUNE CELLS WITH DNMT3A GENE MODIFICATIONS AND METHODS RELATED THERETO

CROSS-REFERENCE TO RELATED APPLICATIONS

This application is a division of U.S. application Ser. No. 15/773,783 filed May 4, 2018 that granted as U.S. Pat. No. 11,020,430 on Jun. 1, 2021, which is the National Stage of International Application No. PCT/US2016/060627 filed Nov. 4, 2016, which claims the benefit of priority to U.S. Provisional Application No. 62/250,546 filed Nov. 4, 2015. The entirety of each of these applications is hereby incorporated by reference for all purposes.

STATEMENT REGARDING FEDERALLY FUNDED RESEARCH

This invention was made with government support under AI030048 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 13081PCT_ST25.txt. The text file is 2 KB, was created on Nov. 4, 2016, and is being submitted electronically via EFS-Web.

BACKGROUND

Chemotherapy is the standard of care for the treatment of many types of cancer, and alternatives methods for treating cancer are need in situations where chemotherapy is not effective. The human immune system is sometimes able to prevent or slow the growth of cancerous cells through recognition by T cells. In order to improve the ability of immune cells to kill cancerous cells, T cells can be isolated from the blood of a patient and genetically altered to specifically bind proteins expressed on the surface of cancerous cells. When put back into the patient, the modified cells more efficiently target the cancerous cells. CD19 is a protein expressed on certain cancerous hematological cells. Brentjens et al. report that T cells altered to bind CD19 can induce remissions of cancer in adults with chemotherapy-refractory acute lymphoblastic leukemia. Sci Transl Med, 2013, 5(177):177ra38. See also Maude et al., Chimeric antigen receptor T cells for sustained remissions in leukemia, N Engl J Med, 2014; 371: 1507-17.

DNA methylation typically occurs at cytosine in cytosine guanosine dinucleotides (CpG) within the DNA of mammals and is broadly used during cellular differentiation to repress transcription. During DNA replication an acquired methylation propagates from parental cells to daughter cells. The heritable quality of DNA methylation programming has provided the basic rationale for epigenetic regulation and maintenance of tissue and cell-specific transcriptional programming. Mammalian DNA methylation is predominantly catalyzed by DNA methyltransferases (Dnmt). Scharer et al. report DNA methylation remodeling accompanies CD8 T cell effector function. J Immunol, 2013, 191(6):3419-29. See also Youngblood et al., Chronic virus infection enforces demethylation of the locus that encodes PD-1 in antigen-specific CD8+ T cells. Immunity, 2011, 35, 13; Yang et al. Dnmt3a in hematological malignancies. Nature reviews Cancer, 2015, 15, 152-165; Youngblood et al., Memory CD8 T cell transcriptional plasticity, F1000Prime Rep, 2015, 7:38; and Ferreira et al. DNMT3A mutations mediate the epigenetic reactivation of the leukemogenic factor MEIS1 in acute myeloid leukemia. Oncogene. 2015.

References cited herein are not an admission of prior art.

SUMMARY

This disclosure relates to the genetic modification of DNMT3A gene in immune cells. In certain embodiments, the modified immune cells may be used in adoptive T cell therapies to enhance immune responses against cancer or chronic infections. In certain embodiments, the disclosure relates to deleting, changing, or inserting nucleotides within the DNMT3A gene in immune cells, e.g., human CD8 T cells, such that the DNMT3A gene product does not function for methylation. In certain embodiments, modification of the DNMT3A gene provides an improvement in antigen-specific T cell functions and/or an enhancement of the longevity of the cells.

In certain embodiments, methods for DNMT3A modification include the use of zinc-finger nucleases, CRISPR/Cas systems, or TALEN nucleases in order to institute sequence specific or non-specific double strand breaks. Although it is not intended that embodiments of this disclosure be limited by any particular mechanism, it is believed that nonhomologous end joining (NHEJ) or homology-directed repair (HDR) mechanisms in the cells results in nucleotide alterations, insertions, or deletions that disrupt gene expression.

In certain embodiments, the disclosure contemplates that the modified DNMT3A T cells are also engineered to express a chimeric antigen receptor (CAR) specific to a cancer or chronic pathogen, and the modified DNMT3A CAR-CD8 T cells are transferred into the patient for treatment optionally in combination with immune checkpoint blockade therapies, e.g., PD-1 or PD-L1 antibodies, CTLA-4 antibodies, pidilizumab, alemtuzumab, ipilimumab, ofatumumab, nivolumab, pembrolizumab, rituximab, bavituximab.

In certain embodiments, the immune cells are T cells, B cells, or cells isolated from peripheral blood or bone marrow that express CD3, CD4, and/or CD8. In certain embodiments, the immune cells are natural killer (NK) cells, dendritic cells (DC), macrophages, monocytes, which develop into macrophages, mast cells, granulocytes, basophils, eosinophils, and neutrophils.

In certain embodiments, this disclosure relates to methods of treating cancer or a chronic infection comprising a) collecting immune cells or CD8 T cells from a subject diagnosed with cancer or a chronic infection providing isolated immune cells or CD8 T cells; b) modifying a DNMT3a gene in the isolated immune cells or CD8 T cells such that the DNMT3A gene does not expresses a protein or a non-functional protein is expressed providing an immune cells or CD8 T cells with an non-functioning DNMT3A gene; c) administering or implanting an effective amount of the immune cells or CD8 T cells with an non-functioning DNMT3A gene into the subject diagnosed with cancer or the chronic infection. In certain embodiments, the chronic infection is a viral or bacterial infection.

In certain embodiments, the immune cells or CD8 T cells or CD8 T cells with an non-functioning DNMT3A gene is further mixed with a recombinant vector that encodes a chimeric tumor associated antigen receptor under conditions such that the chimeric tumor associated antigen receptor is capable of expression on the surface of the CD8 T cells and capable of binding the cells having the tumor associated antigen.

In certain embodiments, modifying a DNMT3A gene in the isolated CD8 T cells is done by making a double stranded cut of the DNMT3A gene under conditions such that repair of the double stranded results in a mutation in the DNMT3A gene. In certain embodiments, the mutation results in an insertion, replacement, or deletion of at least one nucleotide. In certain embodiments, the double stranded cut is created by a protein that contains a domain for cutting the DNA, e.g. fokI or other nuclease domains, and one or more domains that specifically bind nucleic acid sequences within the DNMT3A gene such as a zinc finger nuclease, transcription-activator like effector nucleases, or meganuclease. In certain embodiments, the double stranded cut is created by a Cas protein conjugated to a guide RNA.

In certain embodiments, the subject is diagnosed with a hematological cancer. In certain embodiments, hematological cancer is leukemia, lymphoma, or multiple myeloma.

In certain embodiments, the method further comprises administering to the subject an anti-CTLA-4 antibody, anti-PD-1 antibody, anti-PD-L1 antibody, or combinations thereof.

In certain embodiments, the CAR binds a viral associated antigen that is the HIV envelope glycoprotein GP120. In certain embodiments, the subject is diagnosed as infected with an HIV virus and the immune cells or CD8 T cells or CD8 T cells with a non-functioning DNMT3A gene is further modified with non-functioning CCR5 gene.

BRIEF DESCRIPTION OF THE SEVERAL VIEWS OF THE DRAWING(S)

Figure 4A:
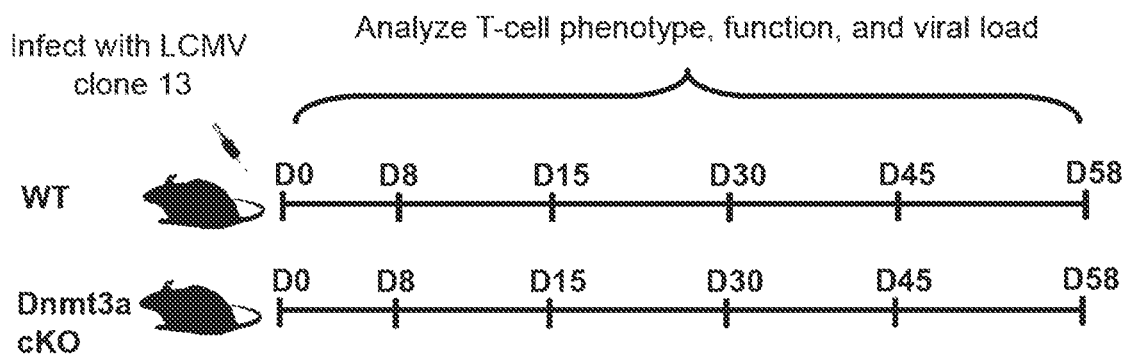

FIG. 4A shows an experimental setup to test whether Dnmt3a conditional deletion in virus-specific CD8 T cells results in heightened control of chronic LCMV infection. WT and Dnmt3a conditional knock out (cKO) mice were infected with the clone 13 strain of LCMV to establish a chronic infection. A longitudinal analysis of antigen-specific CD8 T cell phenotype and serum viremia was performed to assess CD8 T cell differentiation and viral control.

Figure 4B:
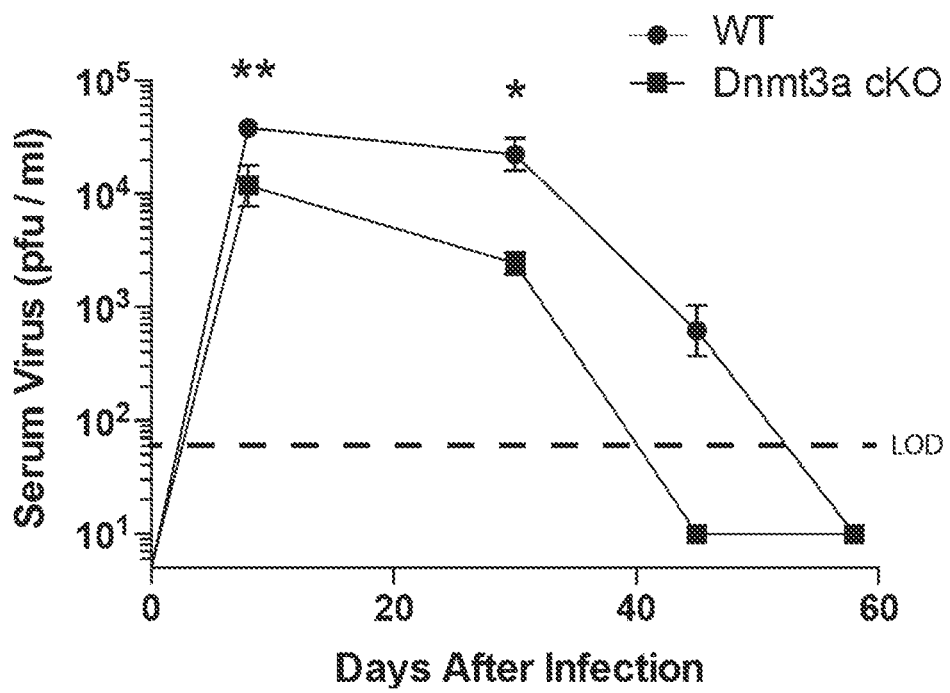

FIG. 4B shows summary graph of serum viral titers. LCMV-specific CD8 T cells were measured longitudinally in WT (blue line) and Dnmt3a cKO (red line) mice PBMC.

Figure 4C:
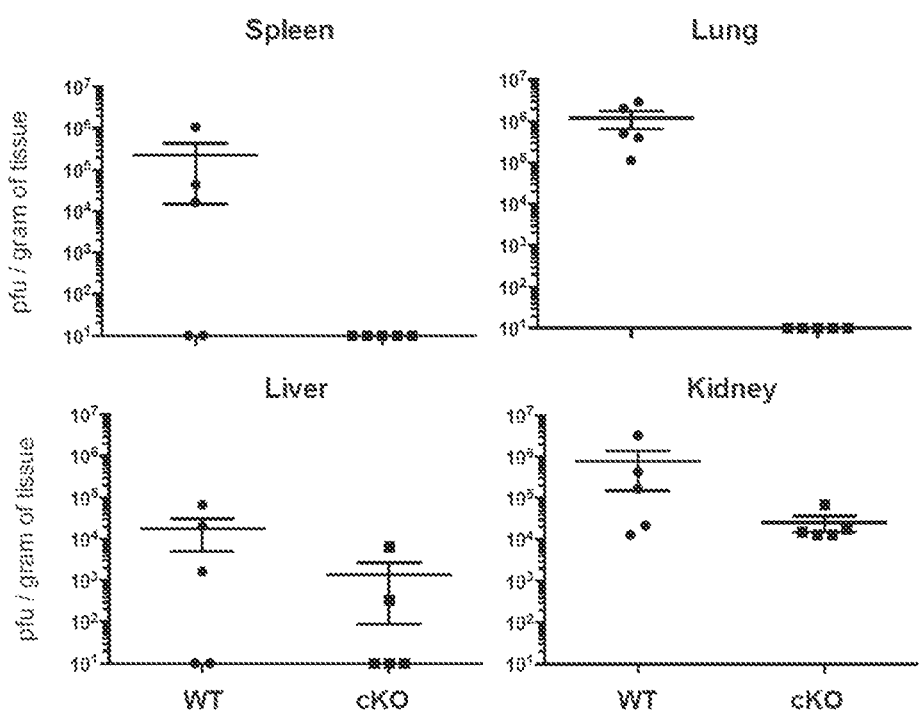

FIG. 4C shows data on tissues 2 months after LCMV Clone 13 infection.

Figure 4D:
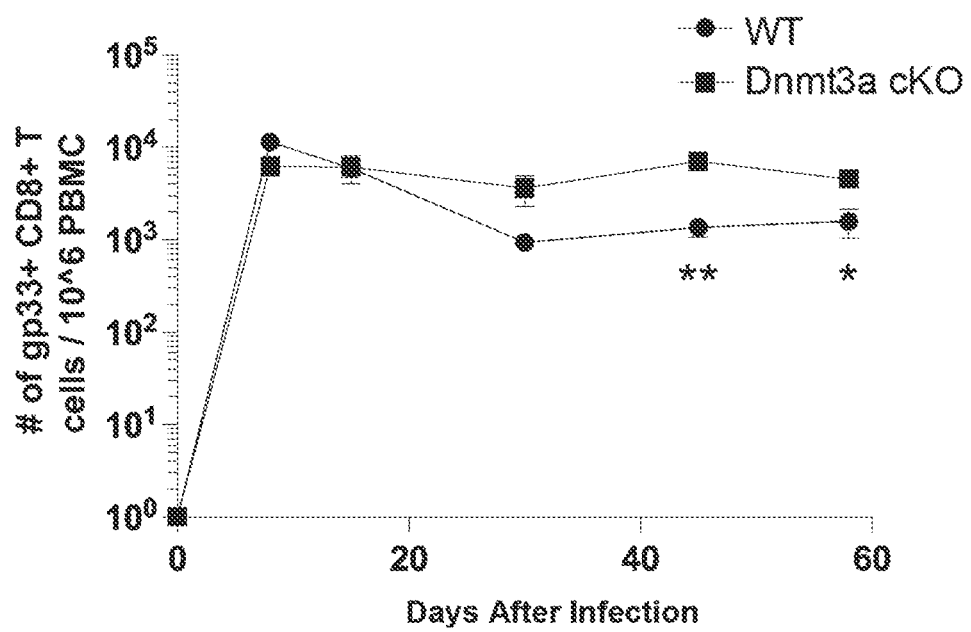

FIG. 4D shows absolute number of antigen-specific CD8 T cells to the LCMV dominant epitopes gp33, gp276, np396 were measured in the spleen at day 58 in WT (blue bars) and Dnmt3a cKO (red bars) mice.

Figure 4E:
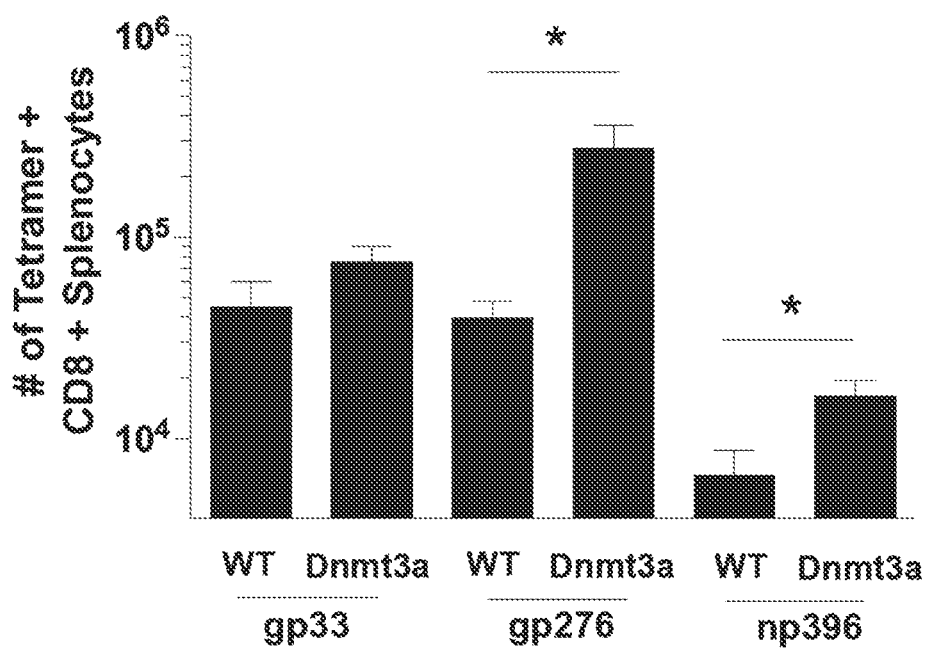

FIG. 4E shows a histogram analysis of markers indicative of antigen-exposure (PD-1), and memory differentiation (CD127 & CD62L) on naïve (gray filled) and LCMV-specific CD8 T cells from WT and Dnmt3a cKO splenocytes at 58 dpi.

Figure 4F:
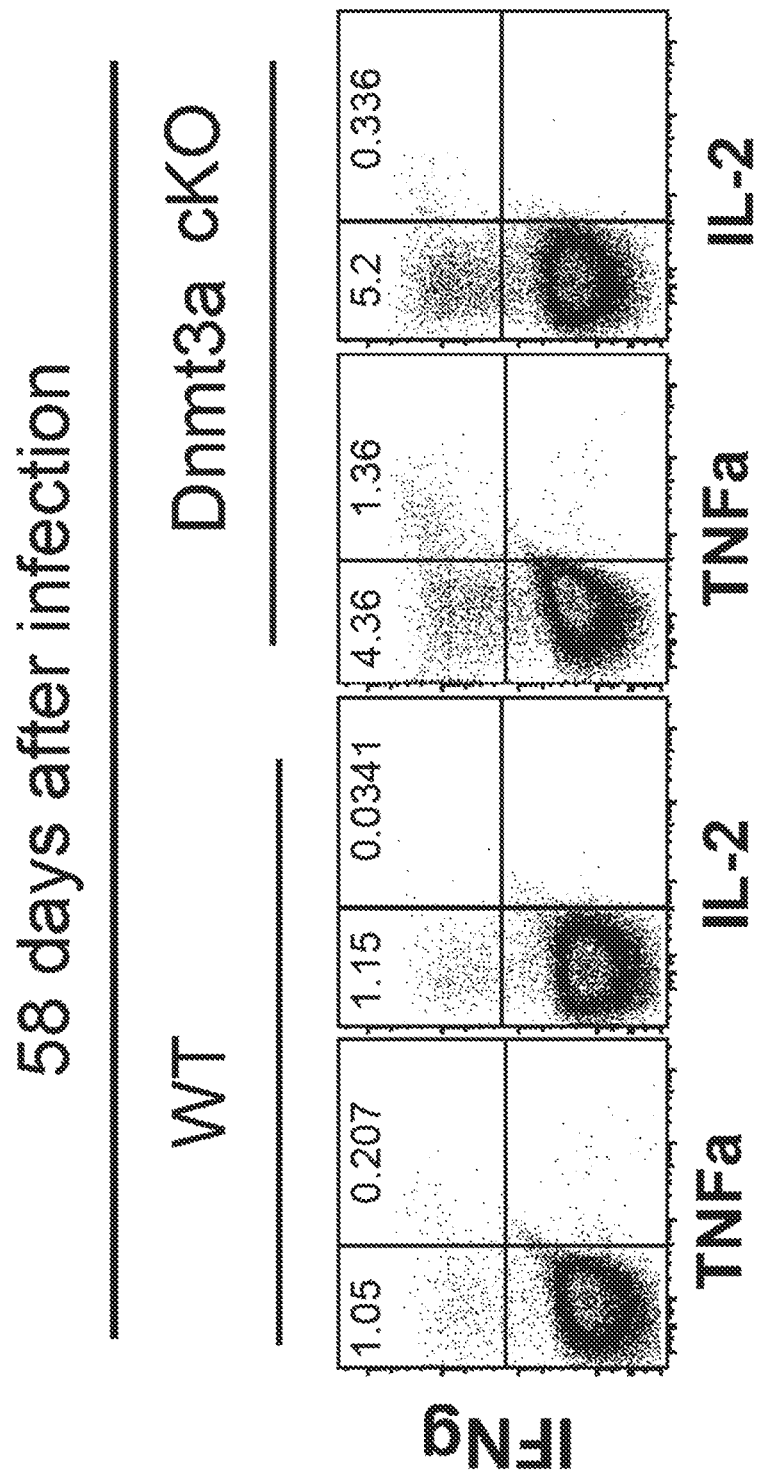

FIG. 4F shows FACS analysis of effector cytokine expression (IFNg, TNFa, and IL-2) from WT and Dnmt3a cKO CD8 T cell splenocytes after a 5 hour ex vivo gp33 peptide stimulation.

Figure 4G:
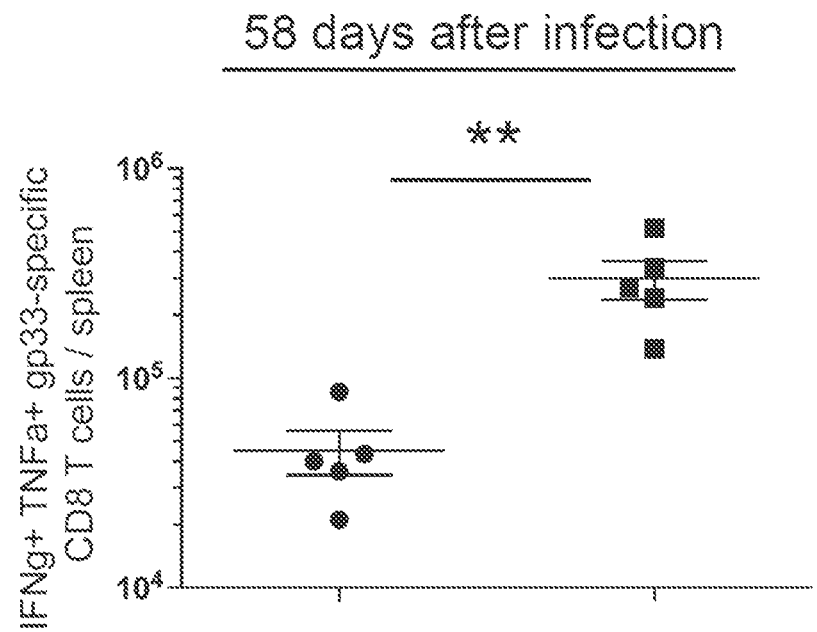

FIG. 4G shows summary graph of the IFNg and TNFa cytokine expression from WT and Dnmt3a cKO gp-33-specific CD8 T cells. N=5 mice per group with 2 replicate experiments.

Figure 4H:
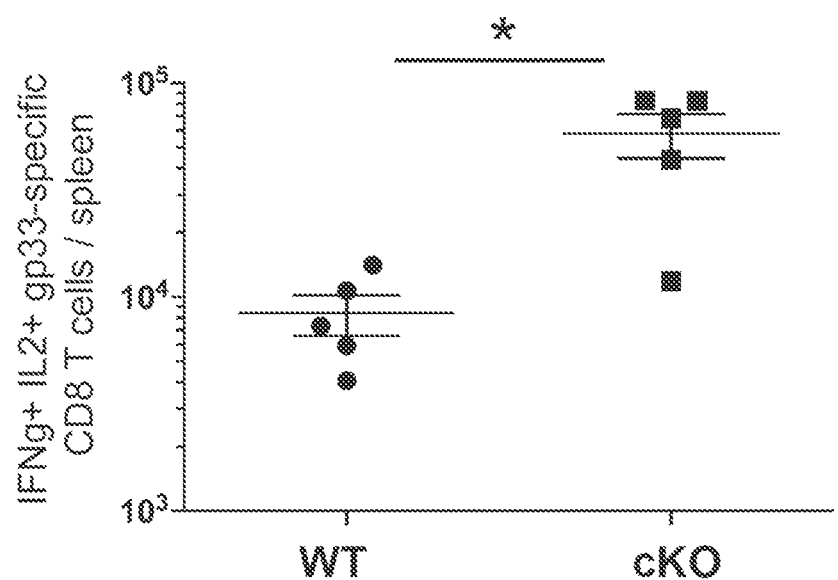

FIG. 4H shows summary graph of the IFNg and IL-2 cytokine expression from WT and Dnmt3a cKO gp-33-specific CD8 T cells. N=5 mice per group with 2 replicate experiments.

Figure 5A:
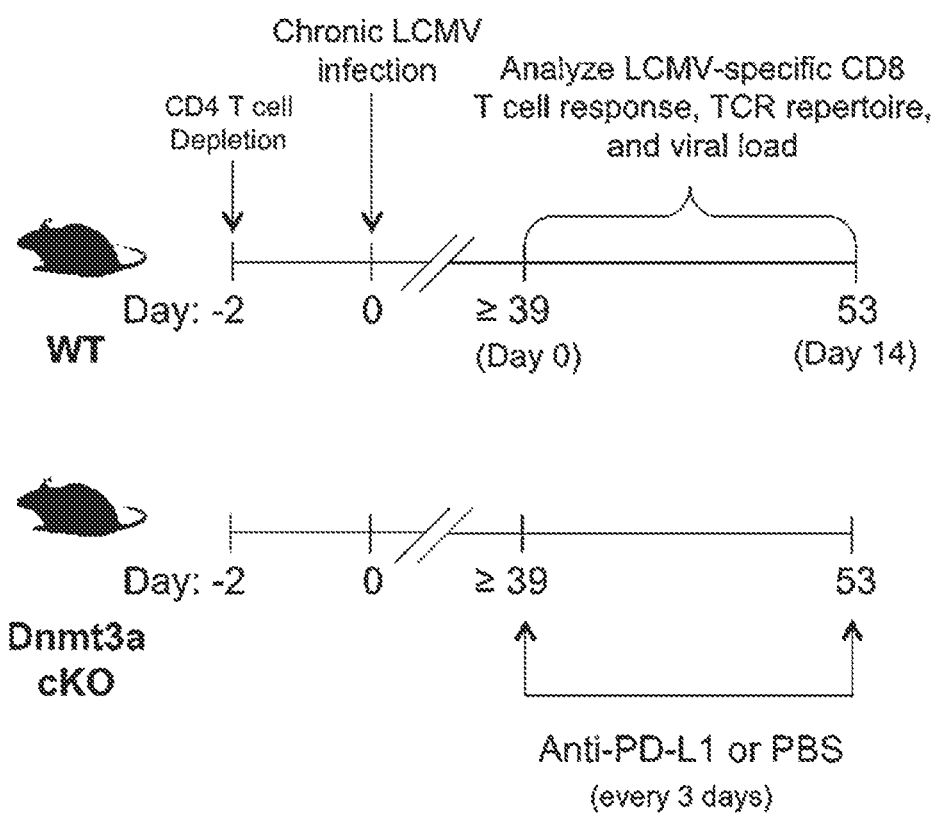

FIG. 5A illustrates an experimental setup. CD4 T cells were depleted in WT and Dnmt3a cKO mice prior to infection with LCMV clone 13, followed by mock or anti-PD-L1 treatment after ≥39 days post-infection for 2 weeks.

FIG. 5B shows FACS analysis data of the three dominant LCMV epitope-specific CD8 T cell populations showing frequencies and fold change in the quantity of gp33, gp276, and np396-specific CD8 T cells from the spleens of mock or anti-PD-L1-treated chronically infected WT (mock-treated: right, PD-1 blockade-treated: left) and Dnmt3a cKO (mock-treated: right, PD-1 blockade-treated: left) mice.

FIG. 5C shows FACS analysis data of IFNg and IL-2 expression from gp33-stimulated CD44hi CD8 T cell splenocytes of mock or PD-1 blockade-treated chronically infected WT and cKO mice. Graphs show fold change in quantity of total IFNg-expressing or IFNg and IL-2 co-expressing CD8 T cells from spleens of mock or PD-1 blockade-treated chronically infected WT and cKO mice. This indicates that inhibition of de novo DNA methylation programming synergizes with PD-1 blockade to enhance antigen-specific CD8 T cell responses and viral control.

FIG. 5D shows data on longitudinal measurement of LCMV titers in the serum.

FIG. 5E shows data on the viral titers in the spleen of chronically infected WT and cKO mice after mock or PD-1 blockade treatment.

FIG. 5F shows data in the liver.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells are observed for a sample compound compared to a control without the compound. It may also be identified by a change in relevant biomarker or gene expression profile, such as PSA for prostate cancer, HER2 for breast cancer, or others.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The term "chimera" when used in reference to a polypeptide of polynucleotide refers to the expression product of two or more coding sequences obtained from different genes, that have been cloned together and that, after translation, act as a single polypeptide sequence such that the single or whole polypeptide sequence, or nucleotide sequence, is not naturally occurring. Chimeric polypeptides are also referred to as "hybrid" polypeptides. The coding sequences include those obtained from the same or from different species of organisms.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar™ software. Variants can be tested in functional assays. Preferred variants have less than 10%, and preferably less than 5%, and still more preferably less than 2% changes (whether substitutions, deletions, and so on).

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, a beta globin polyA signal, SV40 polyadenylation signal, SV40 origin of replication, Col E1 origin of replication, fl origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil.

Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferase I (galT), feedback-insensitive α subunit of anthranilate synthase (OASAID), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxinlike protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}$S or $^{131}$I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the nucleic acids disclosed herein may be a part of any genetic element (vector) which may be delivered to a host cells, e.g., naked DNA, a plasmid, phage, transposon, cosmid, episome, a protein in a non-viral delivery vehicle (e.g., a lipid-based carrier), virus, etc. which transfer the sequences carried thereon. In certain embodiments, a vector may be an adeno-associated virus or human adeno-associated virus (containing AAV genes or sequences) vector, e.g., having nucleic acid sequences derived from AAV1, AAV2, AAV3, AAV4, AAV5, AAV6, AAV7, AAV8, AAV9 serotypes or combinations. The selected vector may be delivered by any suitable method, including intravenous injection, ex-vivo transduction, transfection, electroporation, liposome delivery, membrane fusion techniques, high velocity DNA-coated pellets, viral infection and protoplast fusion.

As used herein, a modified gene is "non-functioning" if the nucleic acid sequence is altered such that an encoded polypeptide product is no longer expressed or if the polypeptide is expressed, then the amino acid sequence is varied or truncated such that the product no longer is able to perform its intended function or interactions with other biomolecules.

De Novo DNA Methylation Establishes T Cells Exhaustion During Chronic Viral Infection Studies herein indicate that CD8 T cells are marked for exhaustion due to cytosine methylation. Although it is not intended that embodiments of the disclosure be limited by any particular mechanism, it is thought that reducing or eliminating the speed of immune cells methylation by DNMT3A will allow the cells to maintain activity for longer periods of time.

Persistent exposure to high levels of antigen during chronic infections results in repression of T cells effector functions. While the pool of antigen-specific CD8 T progressively becomes functionally exhausted, this does not occur uniformly. A significant level of functional heterogeneity exists among the pool of exhausted cells, correlated with the increase of immune inhibitory receptors. It is conceivable that the various subsets of exhausted cells become progressively committed to an exhausted fate and this is coupled to progressive acquisition/reinforcement of de novo DNA methylation programming, i.e., as opposed to DNA methylation inherited from parent cell DNA during replication.

Analyses of changes in gene regulation during T cells exhaustion have specifically identified several inhibitory receptors and transcriptional regulators that mediate T cells exhaustion. Further kinetic analysis of antigen-specific CD8 T cells gene-expression profiles during the early and late stages of chronic infections demonstrated that the cumulative expression of multiple inhibitory receptors, including PD-1 and Tim3, is linked to the progressive decline in effector function during T cells exhaustion. The functional heterogeneity among the pool of exhausted CD8 T cells is demarcated by the combinatorial expression of multiple inhibitory receptors, which in part promote the maintenance of the nonfunctional. While transcriptional, phenotypic, and functional profiling studies have identified several cellular and molecular mechanism that promote T cells exhaustion, the molecular mechanism(s) critical for establishing a stable exhaustion program remain largely unknown.

Gene expression programs established during cellular differentiation are often maintained by covalent alterations to histones and DNA, known as epigenetic modifications. Studies examining cellular commitment during early development have demonstrated that epigenetic modifications provide transcriptional regulatory program that can be propagated during cells division thereby providing a mechanism for maintenance of cellular fates. Genome-wide changes in epigenetic programs are coupled to effector and memory T cells differentiation and some of the DNA methylation programs acquired at the effector stage of the immune response become reinforced during chronic exposure to antigen. Mammalian DNA methylation predominantly occurs at CpG motifs, catalyzed by DNA methyltransferases (Dnmt). Importantly, various malignant cellular transformations have been coupled to specific mutation of the DNMT3A gene.

It is uncertain whether newly acquired DNA methylation programs play a causal role in establishing T cells exhaustion. Since establishment of stable epigenetic programs can be mediated by de novo methyltransferases, the role of DNMT3A programming in the development of T cells exhaustion was investigated.

Methods for DNMT3A Modification in Immune Cells

In certain embodiments, the disclosure contemplates modifying immune cells such that the DNMT3A gene is not able to produce a functioning DNA (cytosine-5)-methyltransferase 3A enzyme that catalyzes the transfer of methyl groups to specific CpG structures in DNA, DNA methylation.

Cells may be obtained by isolation from peripheral blood and optionally purified with fluorescent activated cells sorting e.g., mixing cells with fluorescent antibodies or other fluorescent agents (molecular beacons) and separating the cells by flow cytometry based fluorescent sorting. Another option for cells sorting is to provide magnetic particles that are conjugated to specific binding agents, such as antibodies against a particular antigen on a target cells surface. After mixing with a sample, the antibody bound cells are put through a purification column containing a matrix composed of ferromagnetic spheres. When placed on a magnetic separator, the spheres amplify the magnetic field. The unlabeled cells pass through while the magnetically labeled cells are retained within the column. The flow-through can be collected as the unlabeled cells fraction. After a short washing step, the column is removed from the separator, and the magnetically labeled cells are eluted from the column.

CD3 is expressed on T cells as it is associated with the T cells receptor (TCR). The majority of TCR are made up of alpha beta chains (alpha beta T-cells). Alpha beta T-cells typically become double-positive intermediates (CD4+CD8+) which mature into single-positive (CD4+CD8−) T helper cells or (CD4−CD8+) cytotoxic T cells. T helper cells interact with antigen presenting dendritic cells and B cells. Upon activation with cognate antigen by dendritic cells, antigen-specific CD4 T cells can differentiate to become various types of effector CD4 T cells with specific roles in promoting immune responses. Mature gamma delta T cells are CD4−CD8− double-negative.

T cells may be isolated and separated from a human sample (blood or PBMCs or bone marrow) based on the expression of alpha beta T cells receptor (TCR), gamma delta T cells receptor, CD2, CD3, CD4, CD8, CD4 and CD8, NK1.1, CD4 and CD25 and other combinations based on positive or negative selection.

In certain embodiments, the immune cells are CD8+, CD4+, alpha beta T cells, delta gamma T cells, natural killer cells and/or double-negative alpha beta T cells. Wilhelm et al., report infusion of gamma delta T cells. J Transl Med. 2014; 12: 45. Peripheral blood mononuclear cells (leukapheresis product) were depleted of CD4 and CD8 T-cells using anti-CD4 and anti-CD8 antibodies conjugated to paramagnetic particles. The procedure provides purified gamma delta T cells, NK cells, and double-negative alpha beta T cells.

The modification of a DNMT3A gene may be in the form of deleting, inserting, or altering the nucleotide sequence. For example, a deletion or insertion of one nucleotide in an mRNA coding region would cause the codons for the rest of the sequences to be incorrect. Altering or changing a nucleotide may in result in a stop codon or an amino acid change. Desirable alterations are those that are amino acids that participate in the active cites of the enzyme or in known binding domains. In humans, DNMT3A gene is on chromosome 2. ADDz is the active catalytic domain of Dnmt3a. In certain embodiments, the disclosure contemplates that the genetic alteration is in the ADDz domain.

Non-homologous end joining (NHEJ) is a pathway for double-strand break (DSB) repair in mammalian cells. As NHEJ is not dependent on the cells cycle, DSBs can be repaired via NHEJ in quiescent cells. In certain embodiments, genome editing entails genetic modification via the induction of a double-strand break (DSB) in a specific genomic target sequence, followed by the generation of desired modifications during subsequent DNA break repair. Modifications include gene disruption (the targeted induction of minor insertions and deletions), 'gene correction' (the introduction of discrete base substitutions specified by a homologous donor DNA construct) and targeted gene addition (the transfer of entire transgenes into a native genomic locus).

Strategies for modifying the DNMT3A gene such that may include use of zinc-finger nucleases (ZFNs), transcription activator-like endonucleases (TALENs), and CRISPR-associated Cas9 endonucleases. ZFN have a FokI cleavage domain. Repeating zinc fingers are on both sides of the FokI. The zinc fingers specifically bind target nucleotide sequences. Combinatorial techniques can be used to produce zinc fingers that bind any nucleotide sequence. Fok I cleave the bases that separate the zinc fingers.

Transcription activator-like effector nucleases (TALENs) also contain a FokI nuclease domain fused to a DNA-binding domain. This DNA-binding domain is composed of highly conserved repeats derived from proteins that are secreted in bacteria. See Reyon et al. FLASH assembly of TALENs for high-throughput genome editing. Nature Biotech. 30, 460-465 (2012).

Clustered regularly interspaced short palindromic repeats (CRISPR)-associated Cas9 (CRISPR/Cas9) systems may be engineered into vectors that function in human cells. The Cas9-crRNA complex introduces a double-strand break at a specific site in DNA containing a sequence complementary to crRNA. DNA cleavage is executed by the Cas9 protein. The RuvC and HNH domains generate nicks on opposite DNA strands. The Cas9-crRNA complex functions as an RNA-guided (gRNA) endonuclease with RNA-directed target sequence recognition and protein-mediated DNA cleavage. The gRNA can be altered in order to direct a DNA double-strand break (DSB) (from Cas9 endonuclease expressed in the cells) at a desired genomic location. Protospacer-adjacent motifs (PAMs) are short sequences that are typically required for Cas9 and the gRNA sequence to template the cleavage. *Streptococcus pyogenes* Cas9 can target sites flanked by 5'-NGG sequence.

In certain embodiments, the gene modification is within the DNA that encodes the ADDz domain e.g., (SEQ ID NO: 2)
GTGGAGGTGC<u>AGAACAAGCCC</u>ATGATTGAATGGGCCCTGGGGGCT

TCCAGCCTTCTGGCCCTAAGGGCCTGGAGCCACCAGAAGAAGAGAAGAAT

CCCTACA<u>AAGAAGTGTACACGGA</u>CATGTGGGTGGAACCTGAGGCAGCTGC

CTACGCACCACCTCCACCAGCC<u>AAAAAGCCCC</u>GGAAGAGCACAGCGGAGA

AGCCCAAGGTCAAGGAGATTATTGAT<u>GAGCGCACAAGAGAGCGGC</u>TGGTG

TAC<u>GAGGTGCGGCAGAAGTGC</u>CGGAACATT<u>GAGGACATCTGCATCTCCTG</u>

TGGGAGCCTCAATGTTACCCTGGAACACCCCCTCTTCGTTGGAGGAATGT

GCCAA<u>AACTGCAAGAACTGCTTTCT</u>GGAGTGTGCG.

Underlined segments are portions that could be targeted by *Streptococcus pyogenes* Cas9.

DSBs, e.g., either by Cas9/gRNA or zinc finger nucleases (ZFNs), activate endogenous DNA repair processes such as non-homologous end joining (NHEJ) or homology-directed repair (HDR), to reform double-stranded DNA. Nicking only one strand of DNA may reduce cellular toxicity due to nonhomologous end joining (NHEJ) rates. Cas9 mutants in one of the RuvC or HNH domains may result in a nickase, e.g., Cas9D10A is mutant that is known to function as a nickase.

Identify cells with DNA cleavage can be achieved by exploiting the tendency of certain viruses to preferentially integrate at sites of double-strand breaks. An endonuclease is expressed in cultured human cells, creating double-strand breaks in the DNMT3A gene. Cells are then exposed to a virus that preferentially integrates at double-strand breaks. Genomic DNA sequences containing integrated virus are then identified through selection or direct DNA sequencing.

Chimeric Antigen Receptors

Antigen-specific CD8 T cells play an important role in controlling chronic infections or cancer but progressively lose their functions during prolonged antigen exposure. Such exhaustion of T cells limits the ability of the immune system to fully clear chronic infections or eradicate tumors. Recent approaches to restore CD8 T cells immune responses, such as engineering functional T cells with tumor-specific chimeric antigen receptors (CAR) or immune checkpoint blockade improve the lifespan of certain patients with cancer.

CD19-CARs are indicated to be therapeutically effective at controlling lymphocytic leukemia. However, the modified T cells progressively lose their potency as they experience prolonged exposure to antigen. Thus, there is a need to extend the potency of CD19-CARs by blocking T cells exhaustion. Thus, in order to address T cells exhaustion, DNMT3A from FACS purified donor T cells may be deleted in cells engineered to express the chimeric antigen receptor.

The CAR is typically made up of an antigen-binding polypeptide sequences conjugated to one or more intracellular T-cell signaling domains. A preferred CAR molecule contains the antigen binding domain, an intracellular T cells signaling domain, e.g., the immunoreceptor tyrosine-based activation motif of the CD3-zeta chain, and optionally additional signaling domains within the CAR construct, such as a CD28, CD137 (4-1BB) costimulatory signaling domains. For preparation, T cells may be transduced with lentiviral vector encoding a tumor associated chimeric antigen receptor. The antigen-binding portion may be a single-chain variable fragment derived from a monoclonal antibody that binds the tumor associated antigen or receptors consisting of heavy and light antibody chains fused to a T cells signaling molecule capable of activating the T cells response.

Peripheral blood mononuclear cells (PBMCs) may be isolated by leukapheresis. T cells can be enriched by mononuclear cells elutriation and expanded by addition of anti-CD3/CD28 coated paramagnetic beads for activation of T cells. A lentiviral vector encoding the tumor associated chimeric antigen receptor may be added at the time of cells activation. Cells may be expanded, harvested and cryopreserved in infusible medium sometime after the subject has had an allogeneic stem-cell transplantation.

Suitable tumor associated antigens for targeting includes considerations of the target antigens based on tumor expression on normal tissues. It is preferred to pick optimal target tumor antigens that have no or limited expression on non-cancerous cells. Protein phage display libraries can be generated for testing based on the known sequences of the heavy chain antibodies that bind to antigens.

In certain embodiments, the DNMT3A deficient T cells are engineered to express a chimeric antigen receptor (CAR) specific to an antigen associated with a cancer or chronic pathogen. DNMT3A deficient CAR-CD8 T cells may be adoptively transferred into the patient. Adoptive transfer T cells therapy of DNMT3A deficient CD8 T cells may also be used in combination with immune checkpoint inhibitors such as antibodies to PD-1/PD-L1 and/or CD80/CTLA4 blockade, small molecule checkpoint inhibitors, interleukins, e.g., IL-2 (aldesleukin).

In certain embodiments, the DNMT3A deficient T cells are engineered to express a chimeric antigen receptor (CAR) specific to a neoantigen, a class of tumor associated antigens is formed by peptides that are entirely absent from the normal human genome. For human tumors without a viral etiology, neo-epitopes are created by tumor-specific DNA alterations that result in the formation of novel protein sequences. For virus-associated tumors, such as cervical cancer and a subset of head and neck cancers, epitopes derived from viral open reading frames also contribute to the pool of neoantigens.

A large fraction of the mutations in human tumors is not shared between patients at meaningful frequencies and may therefore be considered patient-specific. Because of this, technologies to interrogate T cells reactivity against putative mutation-derived neoantigens need to be based on the genome of an individual tumor. With the development of deep-sequencing technologies, it has become feasible to identify the mutations present within the protein-encoding part of the genome (the exome) of an individual tumor and thereby predict potential neoantigens.

Treatment of Cancer

In certain embodiments, the modified DNMT3A cells disclosed herein may be used in adoptive T cells therapies to enhance immune responses against cancer. In certain embodiments, this disclosure relates to methods of treating cancer comprising a) collecting immune cells or CD8 T cells from a subject diagnosed with cancer providing isolated immune cells or CD8 T cells; b) modifying a DNMT3a gene in the isolated immune cells or CD8 T cells such that the DNMT3A gene does not expresses a protein or a non-functional protein is expressed providing an immune cells or CD8 T cells with an non-functioning DNMT3A gene; c) administering or implanting an effective amount of the immune cells or CD8 T cells with an non-functioning DNMT3A gene into the subject diagnosed with cancer.

In certain embodiments, the disclosure contemplates that the modified DNMT3A T cells also express a chimeric antigen receptor (CAR) specific to a tumor associated antigen or neoantigen. In certain embodiments, the tumor associated antigen is selected from CD5, CD19, CD20, CD30, CD33, CD47, CD52, CD152(CTLA-4), CD274(PD-L1), CD340(ErbB-2), GD2, TPBG, CA-125, CEA, MAGEA1, MAGEA3, MART1, GP100, MUC1, WT1, TAG-72, HPVE6, HPVE7, BING-4, SAP-1, immature laminin receptor, vascular endothelial growth factor (VEGF-A) or epidermal growth factor receptor (ErbB-1). In certain embodiments, the tumor associated antigen is selected from CD20, CD20, CD30, CD33, CD52, EpCAM, epithelial cells adhesion molecule, gpA33, glycoprotein A33, Mucins, TAG-72, tumor-associated glycoprotein 72, Folate-binding protein, VEGF, vascular endothelial growth factor, integrin αVβ3, integrin α5β1, FAP, fibroblast activation protein, CEA, carcinoembryonic antigen, tenascin, Ley, Lewis Y antigen, CAIX, carbonic anhydrase IX, epidermal growth factor receptor (EGFR; also known as ERBB1), ERBB2 (also known as HER2), ERBB3, MET (also known as HGFR), insulin-like growth factor 1 receptor (IGF1R), ephrin receptor A3 (EPHA3), tumor necrosis factor (TNF)-related apoptosis-inducing ligand receptor 1 (TRAILR1; also known as TNFRSF10A), TRAILR2 (also known as TNFRSF10B) and receptor activator of nuclear factor-κB ligand (RANKL; also known as TNFSF11) and fragments thereof.

In certain embodiments, the T-cells specific to a tumor antigen can be removed from a tumor sample (TILs) or filtered from blood. Subsequent activation and culturing is performed outside the body (ex vivo) and then they are transfused into the patient. Activation may be accomplished by exposing the T cells to tumor antigens.

In certain embodiments, the cancer is selected from multiple myeloma, hepatic cancer, pancreatic cancer, colon cancer, liver cancer, ovarian cancer, breast cancer, gastric cancer, lung cancer, melanoma, skin cancer, ovarian cancer, prostate cancer, head cancer, neck cancer, renal cancer, throat cancer, leukemia, and lymphoma.

In certain embodiments, the method further comprising administering in combination with an anticancer agent selected from gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine, taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, bevacizumab, combretastatin, thalidomide, pomalidomide, and/or lenalidomide or combinations thereof.

In certain embodiments, chemotherapy aimed at depletion of T lymphocytes may be administered about a week before infusion of the CAR T cells.

In certain embodiments, the cancer is a hematological cancer, e.g., leukemia, multiple myeloma, or a lymphoma and administering the combination before or after autologous or allogeneic hematopoietic stem-cell transplantation.

Treatment of Chronic Viral Infections

In certain embodiments, the modified immune cells may be used in adoptive T cells therapies to enhance immune responses against chronic infections. In certain embodiments, this disclosure relates to methods of treating a chronic infection comprising a) collecting immune cells or CD8 T cells from a subject diagnosed with a chronic infection providing isolated immune cells or CD8 T cells; b) modifying a DNMT3a gene in the isolated immune cells or CD8 T cells such that the DNMT3A gene does not expresses a protein or a non-functional protein is expressed providing an immune cells or CD8 T cells with an non-functioning DNMT3A gene; c) administering or implanting an effective amount of the immune cells or CD8 T cells with an non-functioning DNMT3A gene into the subject diagnosed the chronic infection. In certain embodiments, the chronic infection is a viral or bacterial infection.

In some embodiments, the subject is diagnosed with a chronic viral infection. In certain embodiments, the subject undergoes serological monitoring. In some embodiments, the administration is under conditions such that the viral infection is no longer detected. In some embodiments, the subject is diagnosed with a RNA virus, DNA virus, or retroviruses. In some embodiments, the subject is diagnosed with a virus that is a double stranded DNA virus, sense single stranded DNA virus, double stranded RNA virus, sense single stranded RNA virus, antisense single stranded RNA virus, sense single stranded RNA retrovirus or a double stranded DNA retrovirus. In some embodiments, the subject is diagnosed to have a rotavirus, an influenza virus, a herpes virus, a hepatitis virus, or a lentivirus. In some embodiments, titer of the virus in the subject is reduced after the treatment as compared to pre-treatment. In certain embodiments, the subject is a mammal, typically a human.

In certain embodiments, the disclosure relates to methods of treating a subject diagnosed with a viral infection or preventing a viral infection by administration of modified DNMT3A cells disclosed herein. In some embodiments, the subject is diagnosed with influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, 59, parvovirus B19, molluscum contagiosum virus, JC virus (JCV), BK virus, Merkel cells polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella a zoster virus (VZV), Epstein-Barr virus (EBV), cytomegalovirus (CMV), herpes lymphotropic virus, roseolovirus, Kaposi's sarcoma-associated herpesvirus, hepatitis A (HAV), hepatitis B (HBV), hepatitis C (HCV), hepatitis D (HDV), hepatitis E (HEV), human immunodeficiency virus (HIV), The Human T-lymphotropic virus Type I (HTLV-1), Friend spleen focus-forming virus (SFFV) or Xenotropic MuLV-Related Virus (XMRV).

In certain embodiments, the subject is diagnosed with HIV and the DNMT3A modified cells are also modified to provide a non-functioning CCR5 gene. In certain embodiments, the modified cells are autologous CD4 cells. See Tebas et al., report gene editing of CCR5 in autologous CD4 T cells of persons infected with HIV. N. Engl. J. Med., 2014, 370, 901-910.

In certain embodiments, the disclosure contemplates method of treating a subject infected with HIV comprising isolating T cells such as CD4 and/CD8 cells from the subject and modifying DNMT3A and CCR5 genes such that they are nonfunctional optionally in combination with expressing a CAR that binds to an HIV surface antigen, e.g., envelope glycoprotein, GP120, and administering an effective amount of the modified cells to the subject. In certain embodiments, the CD4 cells are modifying with a non-functioning CCR5 gene and the CD8 cells are modified with a non-functioning DNMT3A gene. In certain embodiments, the CD4 and CD8 cells are modifying with a non-functioning CCR5 gene. In certain embodiments, the CD4 and CD8 cells are modifying with a non-functioning DNMT3A gene.

In some embodiments, the disclosure relates to treating chronic tuberculosis by administering modified DNMT3A cells disclosed herein to a subject diagnosed with tuberculosis. In some embodiments, modified DNMT3A cells are administered in combination with another antibiotic.

In some embodiments, the subject is diagnosed with gastroenteritis, acute respiratory disease, severe acute respiratory syndrome, post-viral fatigue syndrome, viral hemorrhagic fevers, acquired immunodeficiency syndrome, or hepatitis.

In some embodiments, the disclosure relates to treating a viral infection by administering modified DNMT3A cells in combination with an antiviral agent. In further embodiments, the subject is co-administered with abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine.

In certain embodiments the disclosure relates to treating a subject with a viral infection after infection by administering modified DNMT3A cells and immunoglobulin.

In certain embodiments, the disclosure relates to treating a viral infection by administering modified DNMT3A cells and a viral vaccine or in the absence of a viral vaccine. In some embodiments, modified DNMT3A cells are administered in the absence of a viral nucleic acid or viral antigen.

In some embodiments, the disclosure relates to the use of modified DNMT3A cells in the production of an anti-viral medicament for the treatment of a viral infection.

EXAMPLES

Inhibition of Dnmt3a De Novo DNA Methylation Programming Prevents T Cells Exhaustion.

Figure 1A:
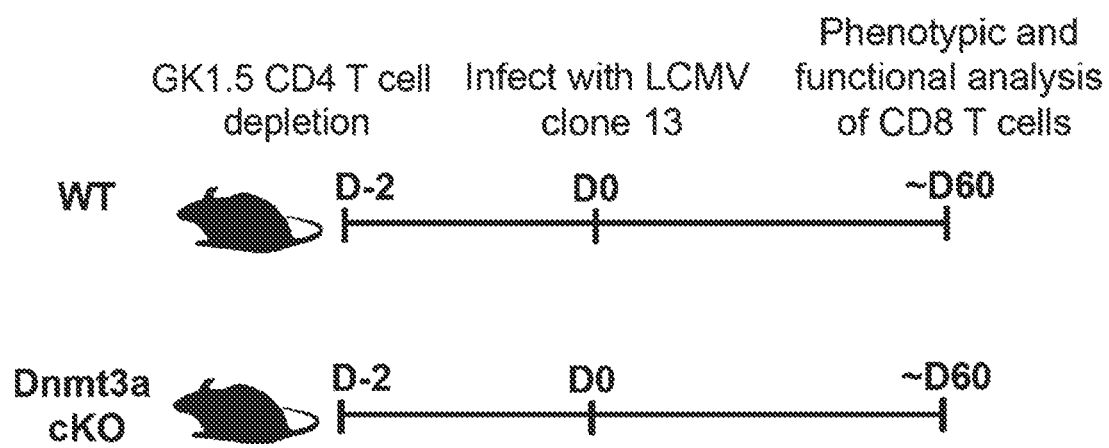
FIG. 1A shows the Experimental setup to test whether Dnmt3a deficient CD8 T cells remain functional during persistent antigen exposure. CD4 T cells were depleted in WT and Dnmt3a conditional knock out (cKO) mice prior to infection with LCMV clone 13.
Figure 1B:
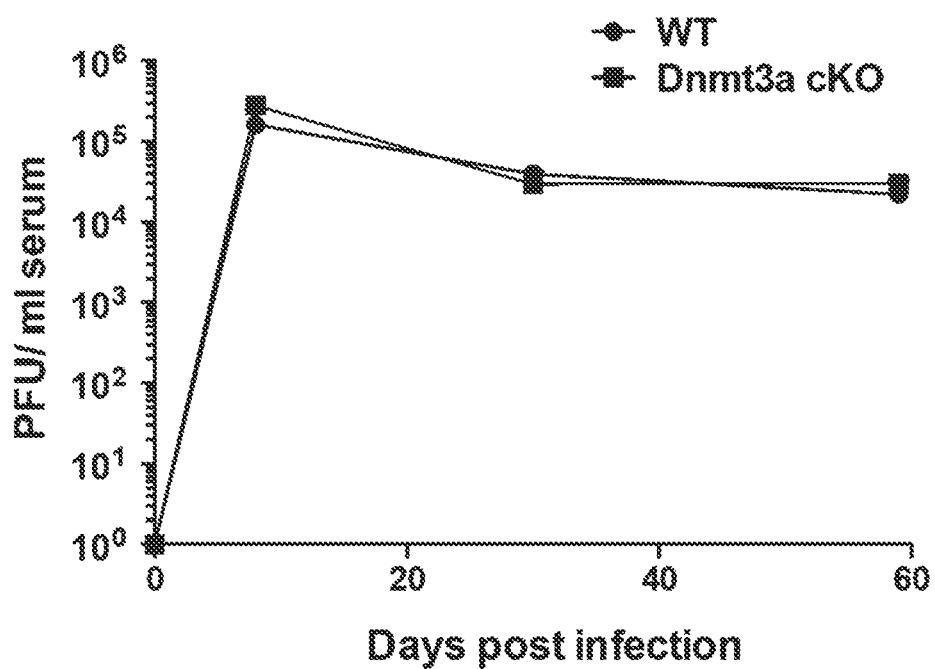
FIG. 1B shows a summary graphs of viral titer in the serum of chronically infected WT and Dnmt3a cKO mice.
Figure 1C:
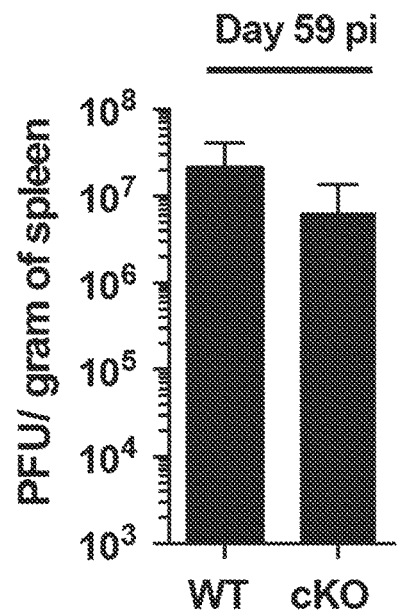
FIG. 1C shows a summary graphs of viral titer in the spleen of chronically infected WT and Dnmt3a cKO mice.
Figure 1D:
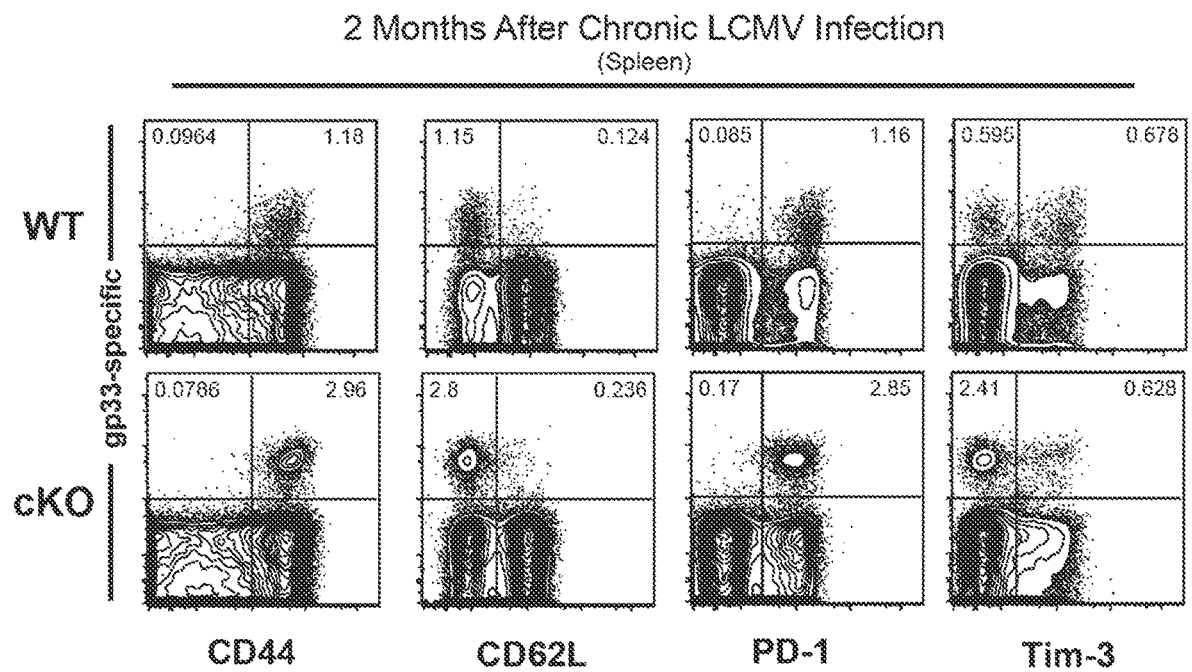
FIG. 1D shows representative FACS analysis of CD44, CD62L, PD-1, and Tim-3 expression on gp33-specific CD8 T cells.
Figure 1E:
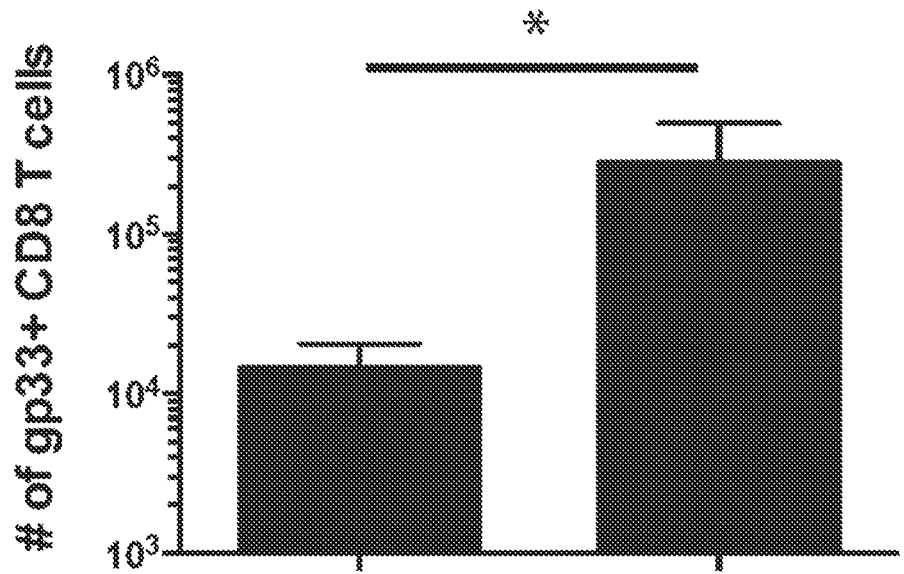
FIG. 1E shows summary graph of gp33-specific CD8 T cell numbers in the spleen of mice after 2 months of chronic LCMV infection.

To gain insight into the impact newly acquired DNA methylation programs have on development of T cells exhaustion, the phenotypic and functional properties of WT and de novo DNA methyltransferase 3a deficient CD8 T cells were examined during persistent exposure to antigen. A conditional deletion strategy employing granzyme b cre driven recombination of Dnmt3a in mice was used to generate Dnmt3a deficient CD8 T cells following TCR ligation. To assess the differentiation of WT and Dnmt3a cKO antigen-specific CD8 T cells in vivo during chronic antigen exposure, the lymphocytic choriomeningitis virus (LCMV) model system of chronic infection was utilized. Prior to infection, CD4 T cells were depleted in WT and Dnmt3a cKO mice to facilitate establishment of a chronic infection with an elevated viral load, which ultimately exaggerates the progression of T cells exhaustion (FIG. 1A). Indeed, equivalently high titers of LCMV were detected in the serum and tissues of both WT and Dnmt3a cKO mice for several months (FIG. 1B, 1C). After two months of persistent viral infection, mice were sacrificed and the quantity, phenotype, and function of the virus specific CD8 T cells were examined. As expected, both WT and cKO antigen-specific CD8 T cells in the persistently infected animals had low levels of CD62L expression. Notably, cKO cells had a moderately higher level of CD44 expression. Importantly, both WT and cKO virus-specific CD8 T cells maintained a high level of expression of the inhibitory receptor PD-1. The maintained expression of PD-1 in the Dnmt3a cKO CD8 T cells from the chronically infected animals indicates that the cKO cells are still experiencing TCR signaling (FIG. 1D). Interestingly though, the cKO cells had lower levels of the inhibitory receptor Tim-3. The quantity of the WT and cKO cells was measured in the tissues of the mice. Unexpectedly, a significantly greater quantity of cKO LCMV-specific CD8 T was observed in the PBMC and spleens of the chronically infected cKO mice. Furthermore, increased quantity of virus-specific CD8 T cells was also observed in the liver and lungs of the cKO mice suggesting that the increase in cells in the PBMC is not due to dysregulation of homing, but rather an overall increase in the quantity of the cells.

Figure 1F:
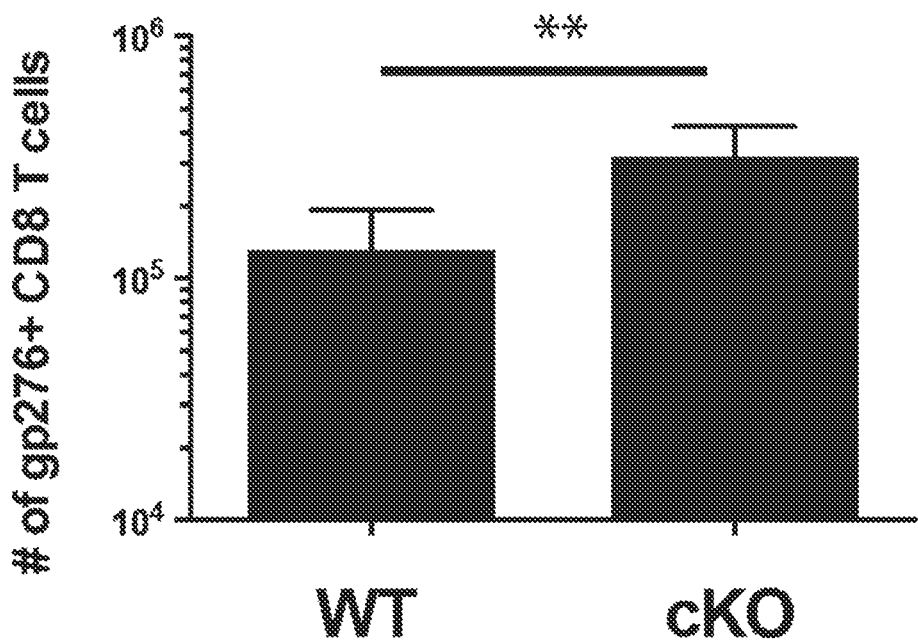
FIG. 1F shows summary graph of gp276-specific CD8 T cell numbers in the spleen of mice after 2 months of chronic LCMV infection.
Figure 1G:
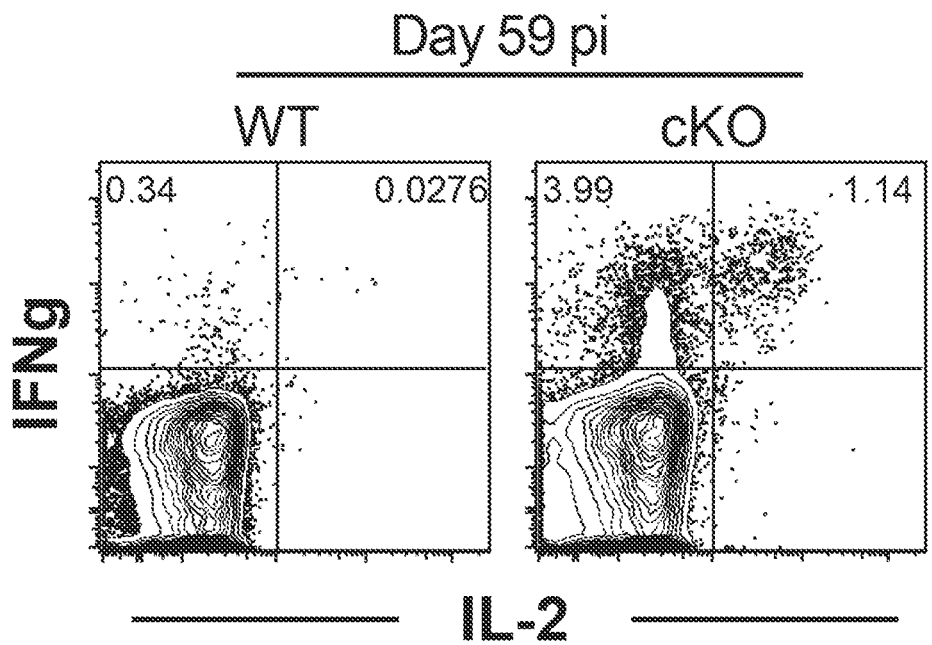
FIG. 1G shows representative FACS analysis of IFNg and IL-2 co-expression from CD8 T cells stimulated with the gp33 peptide.
Figure 1H:
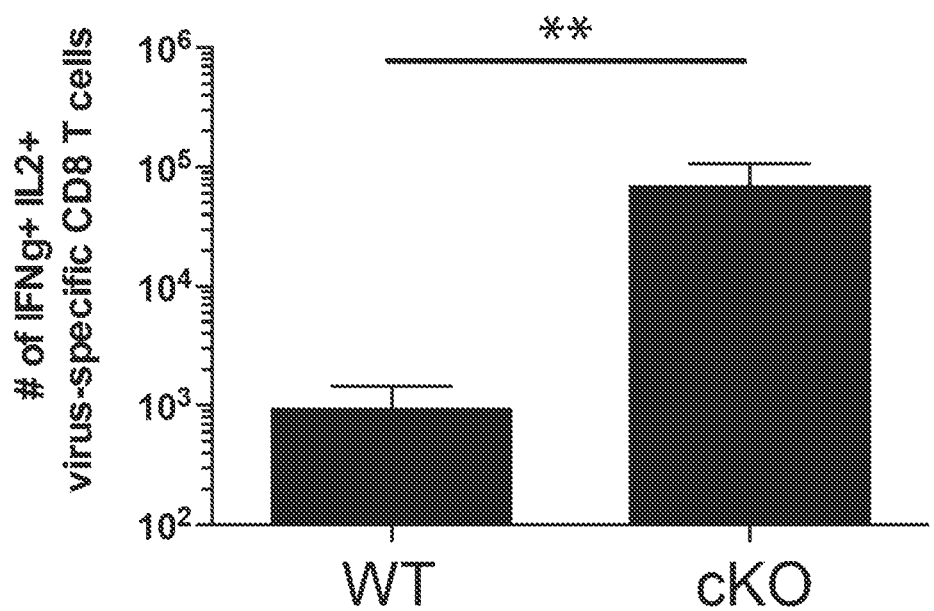
FIG. 1H shows summary graph of IFNg and IL-2 co-expression from CD8 T cells stimulated with the gp33 peptide.
Figure 1I:
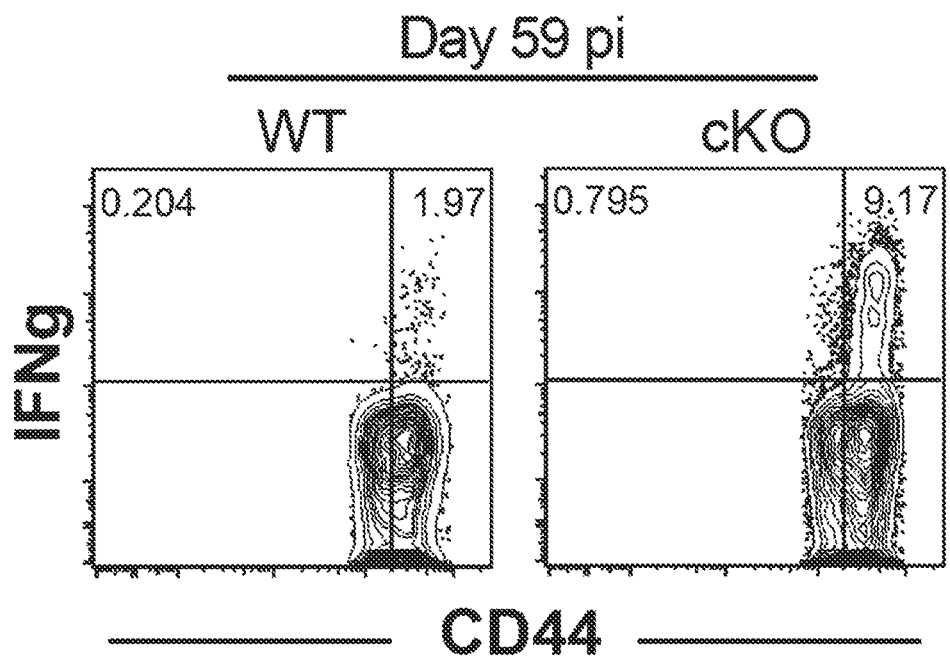
FIG. 1I shows representative FACS analysis of IFNg MFI on ex vivo stimulated CD8 T cells. Summary graphs for cytokine expression was measured following a 5 hr ex vivo stimulation.
Figure 1J:
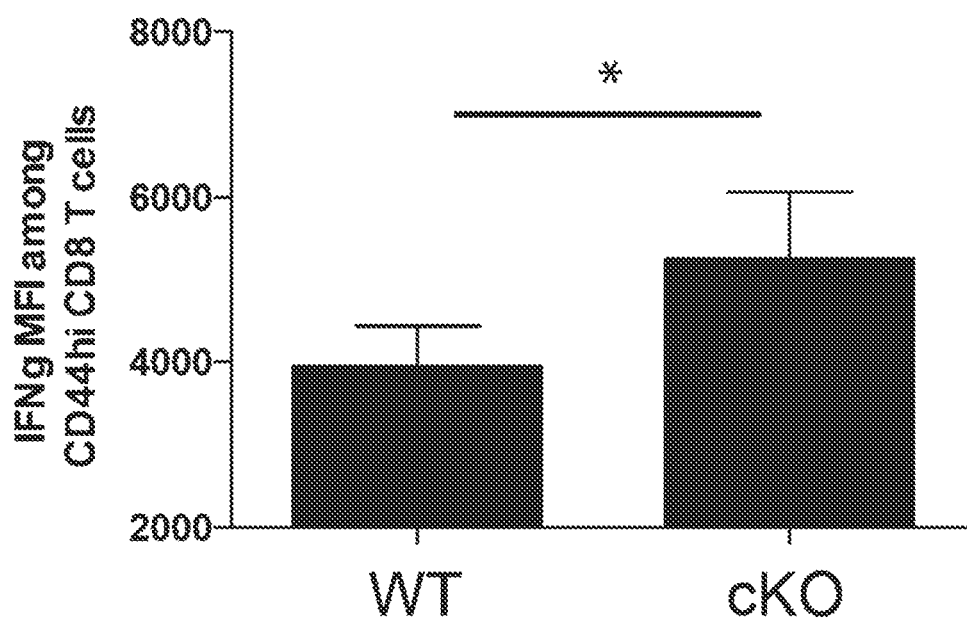
FIG. 1J shows summary graph of IFNg MFI on ex vivo stimulated CD8 T cells. Summary graphs for cytokine expression was measured following a 5 hr ex vivo stimulation.

To further characterize the impact that loss of Dnmt3a programming has on T cells exhaustion, the ability of the Dnmt3a cKO cells to recall the expression of effector cytokines was assessed after ex vivo stimulation. To our surprise, the cKO CD8 T cells had an astonishingly greater quantity of IFNg producing CD8 T cells. Moreover, many of these cells still retained the ability to express IL-2 (FIG. 1F). Previous studies have demonstrated that the pool of exhausted CD8 T cells can be broadly divided into subsets with intermediate and high levels of CD44 expression, and importantly, the CD44hi subset of cells are reported to retain a greater capacity to recall effector functions. Therefore whether the increase in IFNg production was coupled to the increased CD44 expression in the cKO cells was examined. The CD44hi cKO cells had a high level of IFNg+ expression relative the WT CD44hi cells, indicating that on a per-cell basis, cKO antigen-specific CD8 T cells retained a greater functional capacity (FIG. 1G). These data indicate that acquisition of a de novo DNA methylation program is important for establishing functional exhaustion of antigen-specific CD8 T cells. Furthermore, these data indicate that PD-1 expression does not inhibit T cells function when the de novo methylation program is absent.

De Novo DNA Methylation Programming Promotes Differentiation of Fully Exhausted T Cells.

Figure 2A:
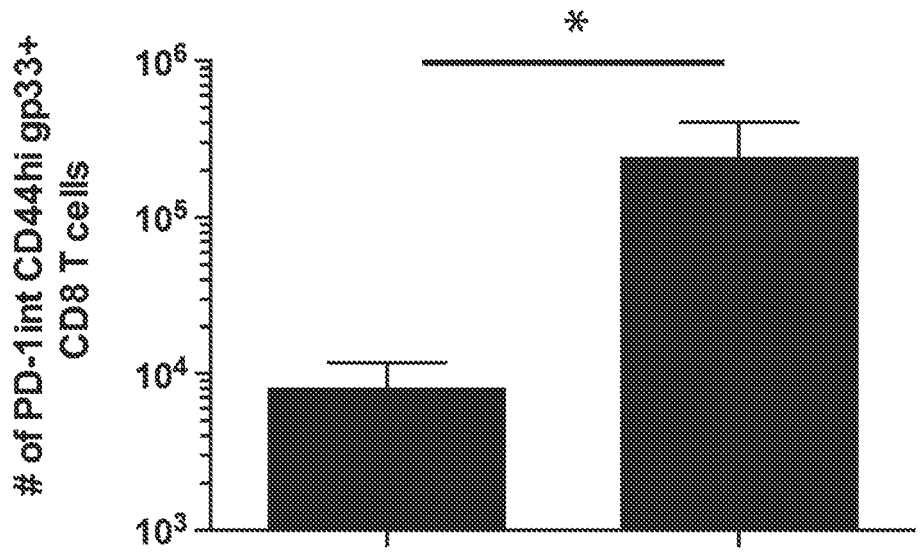
FIG. 2A shows representative and summary graph from FACS analysis of PD-1 and CD44. Co-expression of Inhibitory receptors and transcription factors were measured in gp33-specific CD8 T cells from the spleens of WT and Dnmt3a cKO mice chronically infected with LCMV clone 13 for 59 days.
Figure 2B:
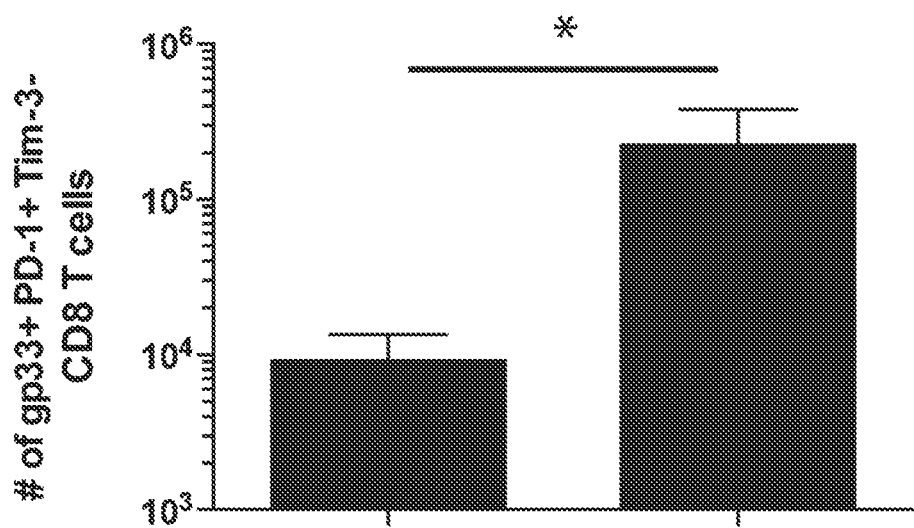
FIG. 2B shows representative and summary graph from FACS analysis of PD-1 and Tim-3. Co-expression of Inhibitory receptors and transcription factors were measured in gp33-specific CD8 T cells from the spleens of WT and Dnmt3a cKO mice chronically infected with LCMV clone 13 for 59 days.
Figure 2C:
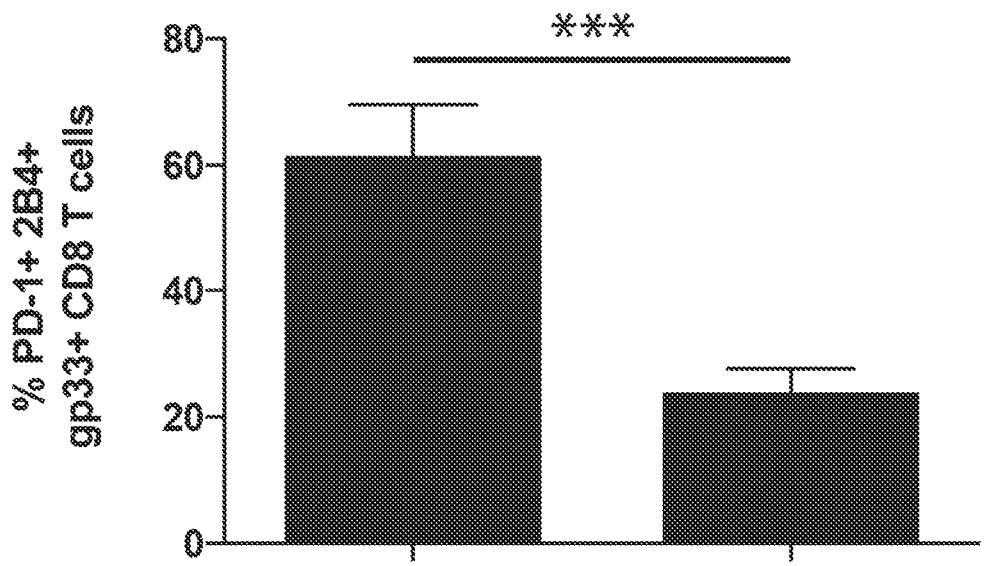
FIG. 2C shows representative and summary graph from FACS analysis of PD-1 and 2b4. Co-expression of Inhibitory receptors and transcription factors were measured in gp33-specific CD8 T cells from the spleens of WT and Dnmt3a cKO mice chronically infected with LCMV clone 13 for 59 days.
Figure 2D:
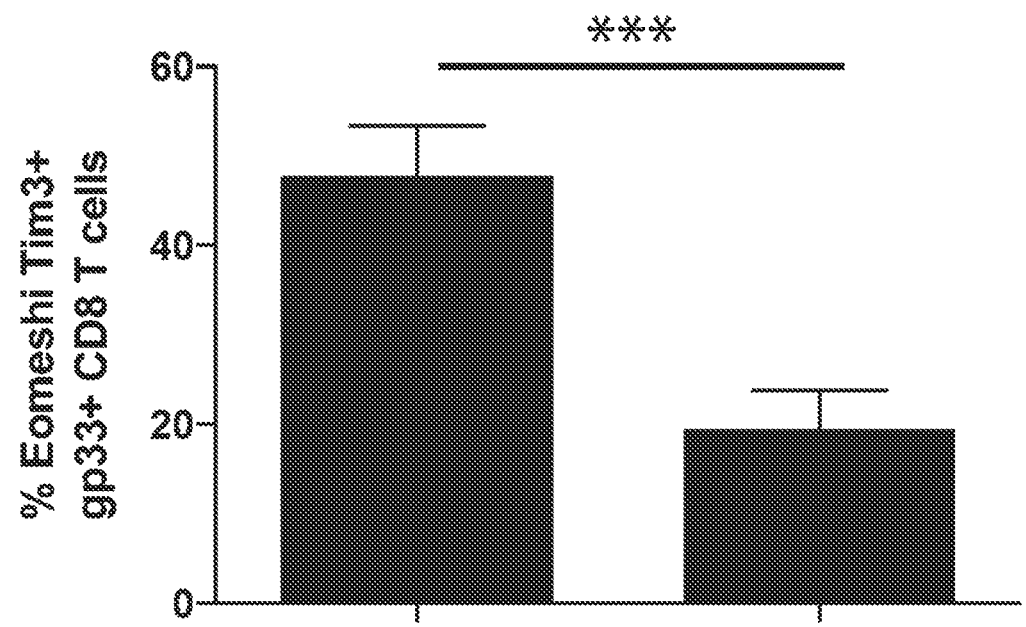
FIG. 2D shows representative and summary graph from FACS analysis of Tim-3 and exomes. Co-expression of Inhibitory receptors and transcription factors were measured in gp33-specific CD8 T cells from the spleens of WT and Dnmt3a cKO mice chronically infected with LCMV clone 13 for 59 days.
Figure 2E:
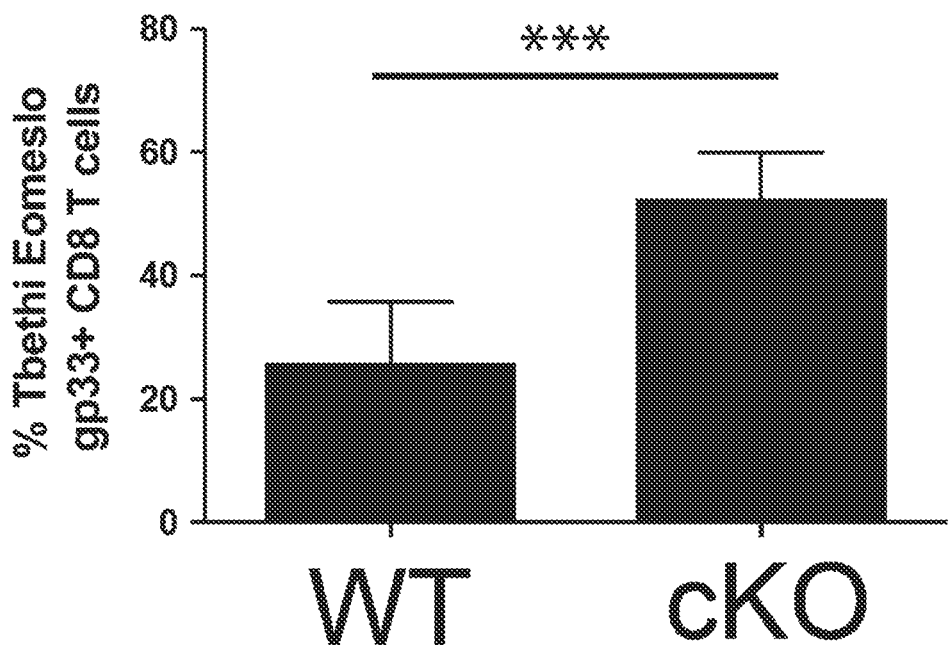
FIG. 2E shows representative and summary graph from FACS analysis of Tim-3 and Tbet. Co-expression of Inhibitory receptors and transcription factors were measured in gp33-specific CD8 T cells from the spleens of WT and Dnmt3a cKO mice chronically infected with LCMV clone 13 for 59 days.

Heterogeneity within the pool of exhausted CD8 T cells has been proposed to arise from a functional adaptation of the cells to the chronic stimulation. Coupled to this adaptation is the progressive co-expression of multiple inhibitory receptors, which contributes to the progressive repression in T cells effector function. The enrichment of CD44hi cKO cells prompted us to further evaluate the expression of inhibitory receptors. Indeed the CD44hi cKO CD8 T cells expressed high levels of PD-1 (FIG. 2A). To further assess the ability of the Dnmt3a cKO CD8 T cells to adapt to their chronic antigen environment, the co-expression of inhibitory receptors Tim-3 and 2b4 was measured. The increased quantity of PD-1+ Dnmt3a cKO antigen-specific CD8 T cells had lower levels of Tim-3 and 2b4 expression (FIGS. 2B & 2C). In addition to co-expression of inhibitory receptors, the gradation of T cells exhaustion has also been reported to be coupled to the dichotomous expression of several transcription factors known to regulate terminal differentiation of T cells. Therefore, the expression of Tbet and eomesodermin expression was examined relative Tim-3 expression. Indeed, the Dnmt3a cKO CD8 T cells had significantly less Eomes expression compared to the exhausted WT cells. Further, the eomes$^{lo}$ cells were predominantly Tim-3− and Tbet+, consistent with results from previous studies that reported upregulation of eomes expression during chronic viral infection was coupled to expression of Tim-3. Paley et al. Progenitor and terminal subsets of CD8+ T cells cooperate to contain chronic viral infection. Science, 2012, 338, 1220-1225. These data indicate that the retained functionality of the Dnmt3a cKO cells is coupled to reduced expression of a transcription factor known to promote terminal differentiation of T cells.

Dnmt3a cKO Cells Maintain a Heightened Capacity for Proliferation.

During prolonged antigen exposure virus-specific CD8 T cells become progressively exhausted and lose the ability to proliferate. Preservation of Dnmt3a cKO CD8 T cells quantity during the prolonged exposure to high levels of antigen prompted further evaluations of the proliferation of the cKO cells during chronic antigen exposure. WT and Dnmt3a cKO mice were depleted of CD4 T cells and then chronically infected with LCMV. Mice were sacrificed at effector and chronic stages of the immune response and the level of Ki67, a marker of cells proliferation, was measured in the virus-specific CD8 T cells. At 8 days post infection, both WT and cKO effector cells had equivalent levels of PD-1+ Tim3+ cells. Additionally, since these cells had recently undergone a burst in antigen-driven proliferation, a majority of the antigen-specific CD8 T cells expressed high levels of Ki67.

Ki67 levels were measured in PD-1+ and Tim3+/− subsets of WT and cKO cells at the chronic stage of the infection. WT virus-specific CD8 T cells undergo a significant reduction in their proliferation following chronic stimulation. Measurement of Ki67 expression among the PD-1 and Tim-3 expressing subsets of cells revealed that the PD-1+ Tim3− have a significant reduction in Ki67 expression. Importantly, the level of Ki67 in Dnmt3a cKO tetramer+ CD8 T cells was higher than WT levels in both the PD-1+ Tim3+ and Tim3− subsets. Further, a greater percentage of Ki67 expressing cells was also observed in the total polyclonal PD-1+ CD8 T cells subsets in the cKO mice versus the WT mice. These data suggest that the elevated quantity of Dnmt3a cKO cells during the persistent viral infection is coupled to their retained proliferative capacity. Collectively, these data indicate that chronic stimulation of antigen-specific CD8 T cells induces a de novo DNA methylation program that enforces an exhaustion program.

Whole-Genome DNA Methylation Profiling of Virus-Specific CD8 T Cells Defines the Dnmt3a Exhaustion Program.

Figure 3A:
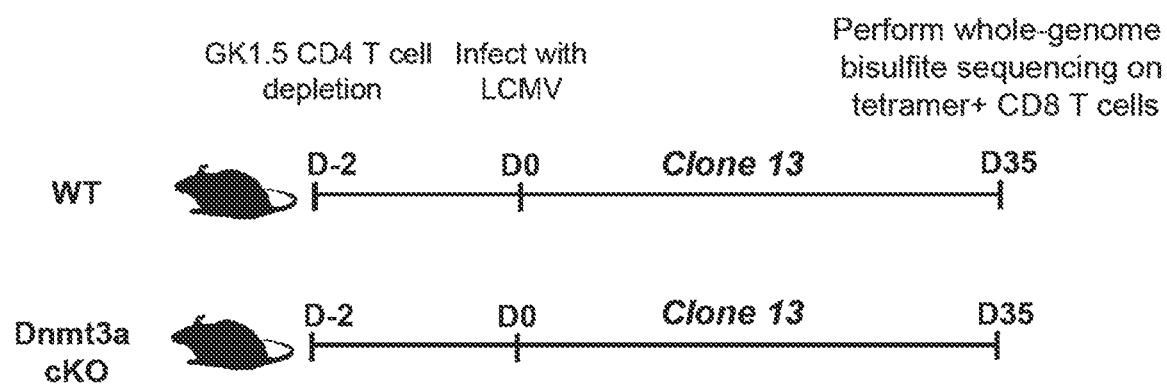
FIG. 3A shows experimental setup for performing whole-genome bisulfite sequencing methylation analysis of virus-specific CD8 T cells. Whole-genome bisulfite sequencing of WT and Dnmt3a deficient CD8 T cells from chronically infected mice.
Figure 3B:
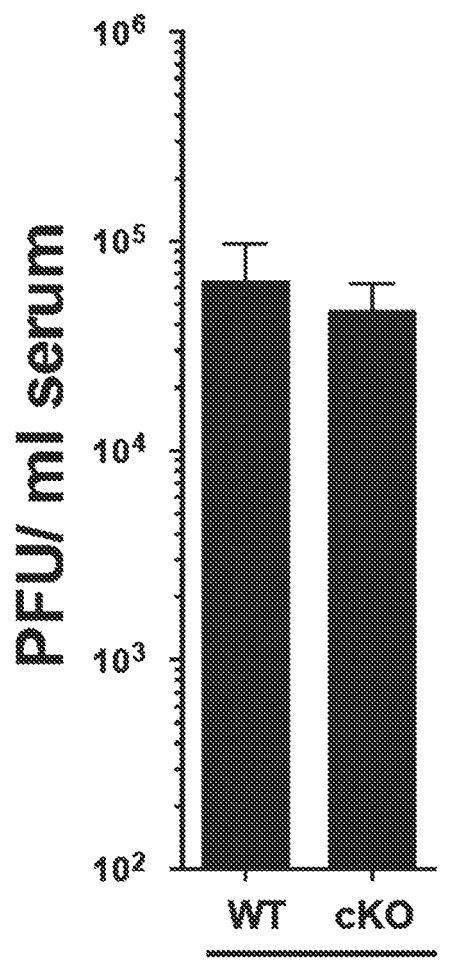
FIG. 3B shows summary graph of serum viral titer from chronically infected mice.
Figure 3C:
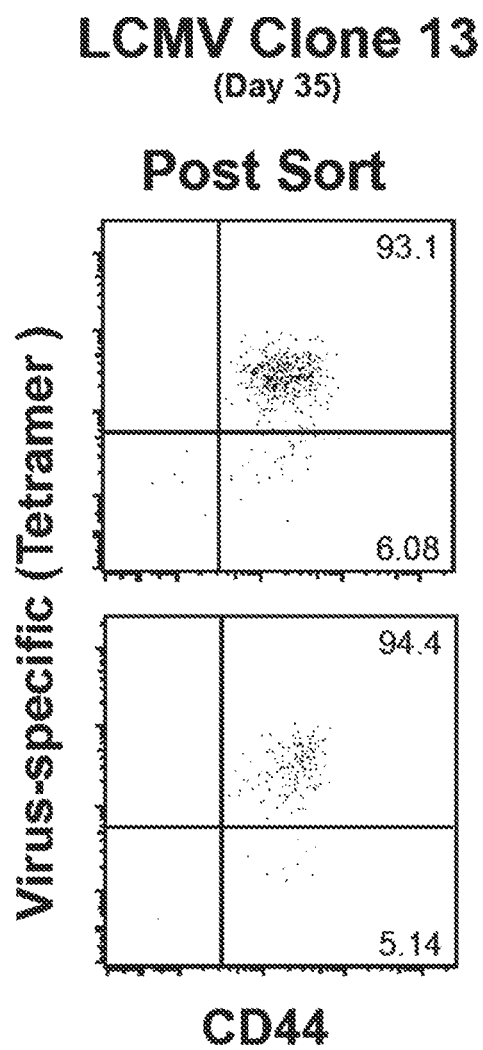
FIG. 3C shows representative FACS analysis of post-sort purity of tetramer+ CD8 T cells.

Our phenotypic and functional characterization of Dnmt3a deficient CD8 T cells undergoing differentiation in the context of a chronic viral infection not only illustrates the biological significance of DNA methylation reprogramming during T cells differentiation, but also indicates that a bona fide de novo DNA methylation program is important for the establishment of T cells exhaustion. Since the gold standard method for measuring changes in DNA methylation is bisulfite sequencing we next proceeded to perform whole-genome bisulfite sequencing (WGBS) of naïve, WT functional memory, WT exhausted, and Dnmt3a cKO non-exhausted (isolated from chronically infected animals) CD8 T cells. WT mice were infected with the acute strain of LCMV to generate functional memory antigen-specific CD8 T cells. In parallel, WT and Dnmt3a cKO mice were depleted of CD4 T cells and then infected with the chronic strain of LCMV (FIG. 3A). Mice were sacrificed 35 days post infection, and genomic DNA was isolated from FACS purified tetramer+CD8 T cells. Again, both WT and Dnmt3a cKO mice retained equally high viral titers (FIG. 3B), but the Dnmt3a cKO antigen-specific CD8 T cells had significantly reduced expression of Tim3 (FIG. 3C). Genome-wide assessment of WT and cKO CD8 T cells revealed that deletion of Dnmt3a did not result in overt changes to the methylation landscape.

Dnmt3a mediates a de novo program at the CD62L promoter, yet techniques to assess the genome-wide methylation profile did not provide the sensitivity or resolution to detect changes in methylation at the 3 CpG sites in the CD62L promoter. In contrast, WGBS analysis reveals that WT exhausted cells have a methylated CD62L promoter while the Dnmt3a cKO cells from the chronically infected animals retain an unmethylated CD62L promoter. These data indicate that WGBS sequencing yielded nucleotide resolution identification of differentially methylated regions in exhausted cells. In addition to detecting the methylated CD62L promoter, it was observed that the perforin and IL-2 loci were heavily methylated in exhausted cells relative to the function WT and Dnmt3a cKO cells. Thus, not only has the WGBS sequencing of these cells provided an epigenetic signature of T cells exhaustion, specific emphasis on Dnmt3a mediated programs establishes methylation programs that are causal in regulating T cells exhaustion.

Inhibition of the Exhaustion De Novo DNA Methylation Program Facilitates Heightened Control of a Chronic Viral Infection.

Given that the Dnmt3a cKO CD8 T cells do not experience a progressive decline in T cells function during the severe-exhaustion model of LCMV infection, whether the heightened function of the CD8 T cells could facilitate viral control under physiological conditions was examined. WT and Dnmt3a cKO mice were infected with the chronic strain of LCMV and their body weight, viral load and antigen-specific CD8 T cells quantity, phenotype and function were measured throughout the course of the infection (FIG. 4A). WT infected animals underwent the characteristic transient decrease in body weight during the effector stage of the immune response, but then recovered from their weight loss at the later stage of the infection. Surprisingly, LCMV clone13 infected Dnmt3a cKO animals experienced only minor weight loss at the effector stage of the immune response. Measurement of serum viral titers revealed that the cKO mice had high viral loads at the effector stage of the immune response, albeit slightly lower than the level of virus in WT infected animals. Quite strikingly though, longitudinal measurement of serum viral load in LCMV clone 13 infected animals revealed a sharp decline in the serum viral load by day 30 after infection in the Dnmt3a cKO mice relative to the WT mice, and was undetectable after 40 days (FIG. 4B). Consistent with the striking decrease in serum viral loads in Dnmt3a cKO mice, the viral load in the lymphoid and non-lymphoid tissues of the cKO mice was much lower compared to WT infected animals (FIG. 4C).

The increased viral control was coupled to maintained T cells quantity and quality. Longitudinal analysis of gp33-specific CD8 T cells in infected cKO animals revealed that the quantity of virus-specific CD8 T cells at the effector stage of the immune response was similar to the quantity of cells in WT animals, but importantly, the cKO antigen-specific CD8 T cells did not undergo the same level of contraction as the WT cells between day 8 and day 30 pi (FIG. 4D). Animals were sacrificed at ~2 months post infection and the quantity, phenotype, and function of the virus-specific CD8 T cells were assessed. Similar to the gp33-specific CD8 T cells, LCMV-specific CD8 T cells recognizing other dominant viral epitopes were present at a higher quantity in the spleens of infected animals (FIG. 4D). Additionally, measurement of the effector cytokine recall response of (IFNg, TNFa, and IL-2) revealed that frequency and number of cytokine producing cells was significantly higher in the cKO mice. Phenotypic examination of the LCMV-specific CD8 T cells 2 months post infection revealed that the Dnmt3a cKO had lower levels of PD-1 expression after viral control (FIG. 4E). Remarkably though, Dnmt3a cKO cells had elevated levels of CD127. Therefore, even though the Dnmt3a cKO experienced prolonged high levels of TCR ligation, they appeared to not retain a transcriptional memory for the exhaustion program. The reduced level of the inhibitory receptor PD-1 and elevated level of CD127 expression suggest that the Dnmt3a cKO virus-specific CD8 T cells may have retained the capacity to develop memory functions. Similar to the greater number of Tetramer+ Dnmt3a cKO cells, the number of IFNg producing cKO cells was also greater than WT cells. Moreover, Dnmt3a cKO cells were also able to express TNFa and IL-2. Thus the combined increase in quantity and retained functionality of the cKO CD8 T cells culminated in heightened control of the clone13 strain of LCMV.

Genetic Deletion of DNMT3a in CD8 T Cells Used for Adoptive T Cells Therapy to Enhance Immune Responses Against Cancer or Chronic Infections.

In one example, autologous CD8 T cells are isolated from peripheral blood mononuclear cells (PBMCs) of patients with B cells neoplasms. Naïve and memory CD8 T cells are FACS purified. CD8 T cells are treated with the commercially available zinc finger nuclease that targets human DNMT3A. Sigma-Aldrich CompoZr™ Knockout ZFNs (NM_175630) create targeted double strand breaks at human DNMT3A (1788). Through the cellular process of Non-Homologous End Joining, this double strand break can result in modification of the DNA sequence and therefore create a functional knockout of the targeted gene. To provide the best chance of creating a functional gene knockout, CompoZr™ Knockout ZFNs are targeted to the first ⅔ of the coding region for the gene of interest. Purified CD8 T cells ($1 \times 10^7$) are treated with the DNMT3a Zinc Finger Nuclease using established techniques. See Perez et al. Nature Biotechnology 26, 808-816 (2008).

In another example, a targeting sequence for gDNA Cas9 creation of double strand breaks in DNMT3 would be

GCATGATGCGCGGCCCA. (SEQ ID NO: 1)

See Mail et al., RNA-Guided Human Genome Engineering via Cas9, Science, 2013, 339(6121): 823-826.

CD19 Expressing Chimeric Antigen Receptors

Autologous CD8 T cells are isolated from the PBMC of patients with B cells neoplasms. Naïve and memory CD8 T cells are FACS purified. CD8 T cells are treated with the commercially available zinc finger nuclease that targets human DNMT3a. DNMT3A deficient CD8 T cells are grown in vitro and transduced with lentiviral vectors containing a CD19-CAR. See Milone et al. Chimeric receptors containing CD137 signal transduction domains mediate enhanced survival of T cells and increased antileukemic efficacy in vivo. Mol Ther 2009, 17:1453-1464. Following in vitro expansion, DNMT3a deficient CD19-CAR T cells are adoptively transferred back in to the patient. Longitudinal analysis of DNMT3A deletion and the CD19 transgene in the adoptively transferred CD8 T cells are measured from the patient PBMC using PCR based methods. Patient tumor burden and clinical responses are monitored.

protein or a non-functional protein is expressed providing CD8 T cells with a non-functioning DNMT3a gene; and c) administering or implanting an effective amount of the CD8 T cells with a non-functioning DNMT3a gene into the subject diagnosed with cancer.

2. The method of claim 1, wherein the CD8 T cells with an non-functioning DNMT3a gene is further mixed with a recombinant virus that encodes a chimeric tumor associated antigen receptor under conditions such that the chimeric tumor associated antigen receptor is capable of expression on the surface of the CD8 T cells and capable of binding the tumor associated antigen.

3. The method of claim 1, wherein the isolated CD8 T cells is further mixed with a recombinant virus that encodes a tumor antigen receptor under conditions such that the tumor antigen receptor is capable of expression on the surface of the CD8 T cells and binding tumor cells.

4. The method of claim 1, wherein modifying a DNMT3A gene in the isolated CD8 T cells is done by making a double stranded cut of the DNMT3A gene under conditions such that repair of the double stranded results in a non-functioning mutation in the DNMT3A gene.

5. The method of claim 4, wherein the mutation results in an insertion, replacement or deletion of at least on nucleotide.

The invention claimed is:

1. A method of treating cancer comprising a) collecting CD8 T cells from a subject diagnosed with cancer providing isolated CD8 T cells;

b) modifying a DNMT3a gene in the isolated CD8 T cells such that the DNMT3a gene does not expresses a 6. The method of claim 4, wherein the double stranded cut is created by a zinc finger nuclease.

7. The method of claim 4, wherein the double stranded cut is created by a Cas protein conjugated to a guide RNA.

8. The method of claim 1, wherein the subject is diagnosed with a hematological cancer.

9. The method of claim 8, wherein the hematological cancer is leukemia, lymphoma, or multiple myeloma.

10. The method of claim 1 further comprising administering to the subject an anti-CTLA-4 antibody, anti-PD-1 antibody, anti-PD-L1 antibody, or combinations thereof.

* * * * *